United States Patent
Morishita et al.

(10) Patent No.: US 8,489,180 B2
(45) Date of Patent: Jul. 16, 2013

(54) FLUORESCENCE OBSERVATION APPARATUS

(75) Inventors: Koki Morishita, Tokyo (JP); Akira Hasegawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 7 days.

(21) Appl. No.: 12/887,679

(22) Filed: Sep. 22, 2010

(65) Prior Publication Data

US 2011/0009702 A1    Jan. 13, 2011

Related U.S. Application Data

(63) Continuation of application No. PCT/JP2010/054314, filed on Mar. 15, 2010.

(30) Foreign Application Priority Data

Mar. 24, 2009  (JP) ................... 2009-072851

(51) Int. Cl.
    *A61B 5/00*  (2006.01)
(52) U.S. Cl.
    USPC ........................................ 600/478
(58) Field of Classification Search
    USPC ............................ 600/478; 382/128
    See application file for complete search history.

(56) References Cited

U.S. PATENT DOCUMENTS

| | | | |
|---|---|---|---|
| 5,751,839 A * | 5/1998 | Drocourt et al. | 382/133 |
| 2002/0197609 A1 | 12/2002 | Danenberg | |
| 2005/0002859 A1* | 1/2005 | Marnett et al. | 424/1.11 |
| 2005/0027166 A1* | 2/2005 | Matsumoto et al. | 600/162 |
| 2007/0270652 A1 | 11/2007 | Morishita et al. | |
| 2009/0216079 A1* | 8/2009 | Morgan et al. | 600/109 |
| 2010/0198048 A1 | 8/2010 | Togawa | |
| 2011/0009702 A1 | 1/2011 | Morishita et al. | |
| 2011/0244501 A1* | 10/2011 | Chu et al. | 435/29 |

FOREIGN PATENT DOCUMENTS

| | | |
|---|---|---|
| CN | 101448450 A | 6/2009 |
| CN | 101801436 A | 8/2010 |
| EP | 2 020 200 A1 | 2/2009 |

(Continued)

OTHER PUBLICATIONS

Kim, et al., "Aberrant Crypt Focus Size Predicts Distal Poly Histopathology", Cancer Epidemiol Biomarkers Prev 2000; pp. 1155-1162, vol. 17(5).

(Continued)

*Primary Examiner* — Jonathan Cwern

(74) *Attorney, Agent, or Firm* — Scully, Scott, Murphy & Presser, P.C.

(57) ABSTRACT

The number of aberrant crypt foci (ACF) can be readily counted without overlooking the existence of ACF to achieve reduced observation time. A fluorescence observation apparatus includes a light source unit inserted into a body cavity of a biological organism and emitting excitation light onto an inner wall of the body cavity; an image acquisition unit that acquires image information by acquiring an image of fluorescence generated when a fluorescent probe whose fluorescence characteristic changes by reacting with a molecule existing in an ACF formed in the inner wall of the body cavity is excited by the excitation light; a position control unit that moves the light source unit and the image acquisition unit relative to the inner wall of the body cavity; and a counting section that counts the number of fluorescence generation sites included in the image acquired by the image acquisition unit.

20 Claims, 17 Drawing Sheets

FOREIGN PATENT DOCUMENTS

| | | |
|---|---|---|
| EP | 2 213 318 A1 | 8/2010 |
| JP | 04-081682 | 3/1992 |
| JP | 07-163572 | 6/1995 |
| JP | 2004-530434 | 10/2004 |
| JP | 2006-141734 | 6/2006 |
| JP | 2007-307278 A | 11/2007 |
| JP | 2008-167922 A | 7/2008 |
| JP | 2009-000118 | 1/2009 |
| JP | 2010-220895 A | 10/2010 |
| WO | WO 02/103055 A1 | 12/2002 |
| WO | 2007/135925 A1 | 11/2007 |
| WO | WO 2008/050255 A1 | 5/2008 |
| WO | 2009/057774 A1 | 5/2009 |
| WO | 2010/110104 A | 9/2010 |

OTHER PUBLICATIONS

International Search Report dated Apr. 13, 2010.
Takayama, et al., The Journal of the Japanese Society of Internal Medicine, Feb. 10, 2007, pp. 220-225, vol. 96, No. 2.
Niitsu, Y et al., The Journal of the Japanese Society of Internal Medicine, Feb. 20, 2007, pp. 41-45, vol. 96, special extra issue.
International Search Report dated Dec. 6, 2011.

* cited by examiner

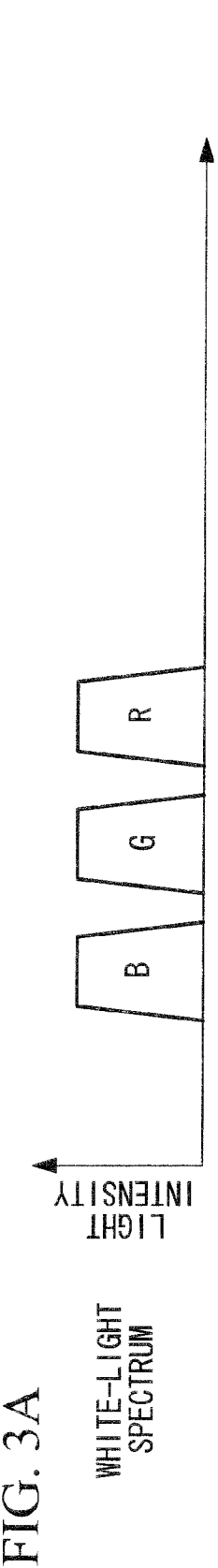
FIG. 3A WHITE-LIGHT SPECTRUM
FIG. 3B EXCITATION-LIGHT SPECTRUM
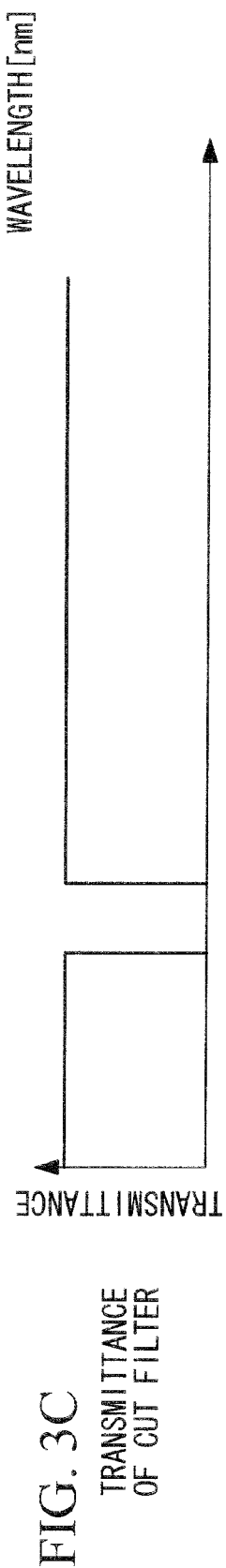
FIG. 3C TRANSMITTANCE OF CUT FILTER
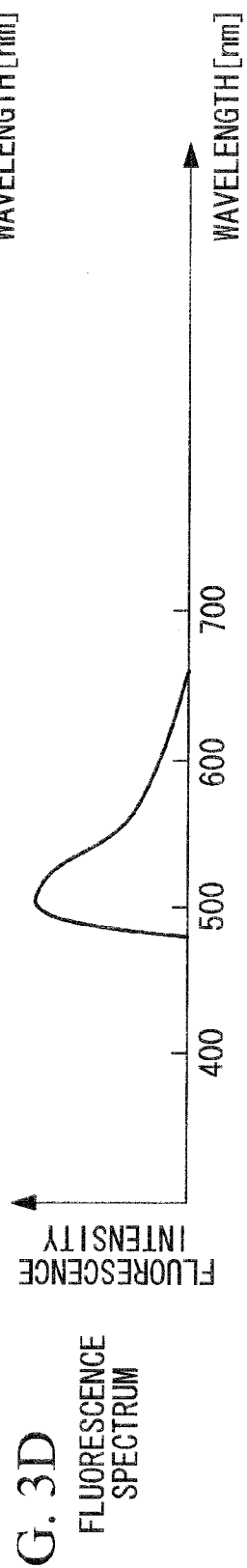
FIG. 3D FLUORESCENCE SPECTRUM

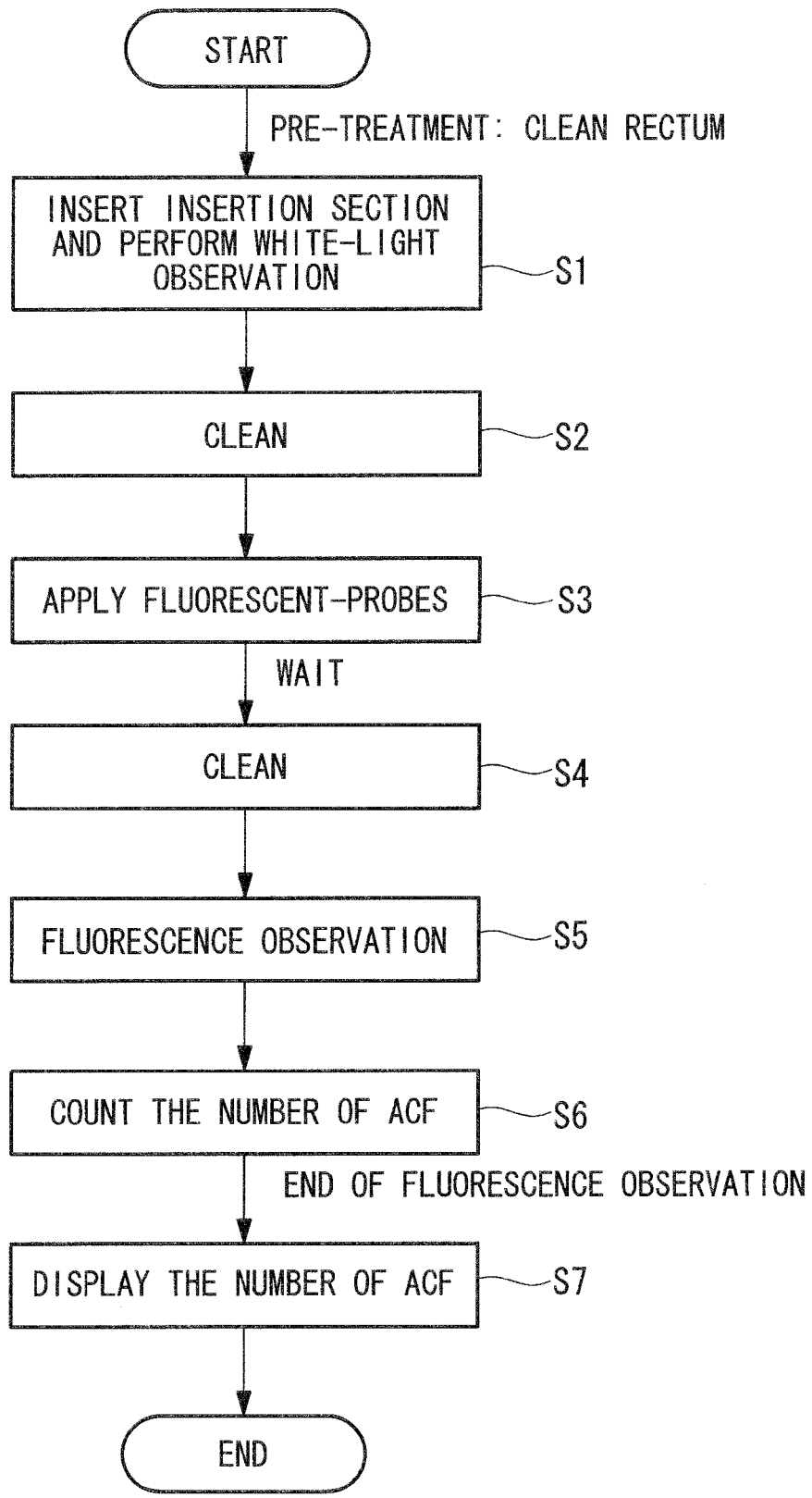

MEASUREMENT SCREEN

ENDOSCOPIC IMAGE

GST-π-SENSITIVE FLUORESCENT PROBES

REFERENCE-DYE FLUORESCENCE SPECTRUM

EXCITATION LIGHT SOURCE A

EXCITATION LIGHT SOURCE B

FLUORESCENCE OBSERVATION APPARATUS

TECHNICAL FIELD

The present invention relates to fluorescence observation apparatus.

BACKGROUND ART

In the related art, research results that have been obtained show that the number and the size of ACF (aberrant crypt foci) formed in recta have a strong correlation with a future incidence of cancer. In such research, a method is employed, in which, for example, the pit pattern is made visible using methylene blue, and the ACF are checked one-by-one while counting the number thereof by using a magnifying endoscope or the like (for example, see Non Patent Literature 1).

CITATION LIST

Non Patent Literature

{NPL 1} Cancer Epidemiol Biomarkers Prev., May 2008; 17(5): 1155-62

SUMMARY OF INVENTION

Technical Problem

However, observing the entire rectum and checking the ACF one-by-one by using a magnifying endoscope or the like as in the related art can be a problem in that the ACF can possibly get overlooked and that the observation time is too long since the observation must be meticulously performed in every corner to prevent the ACF from getting overlooked. Moreover, the definition for determining whether an observed object is an ACF or not depends on the observer's subjective assessment, which is also a problem in that it lacks accuracy.

The present invention has been made in view of these circumstances, and an object thereof is to provide a fluorescence observation apparatus that can readily count the number of ACF without overlooking the existence thereof and that can achieve reduced observation time.

Solution to Problem

In order to solve the aforementioned problems, the present invention provides the following solutions.

An aspect of the present invention provides a fluorescence observation apparatus including an illuminating section that is inserted into a body cavity of a biological organism and that emits excitation light onto an inner wall of the body cavity; an image acquisition section that acquires an image of fluorescence generated by the excitation light emitted from the illuminating section so as to acquire image information; and a counting section that counts the number of fluorescence generation sites on the basis of the fluorescence included in the image information acquired by the image acquisition section, the fluorescence generation sites being generated when a fluorescent probe whose fluorescence characteristic changes by reacting with a molecule existing in an ACF formed on the inner wall of the body cavity is excited or when fluorescent probe whose fluorescence characteristic changes by reacting with a product produced by activation of the molecule is excited.

According to this aspect, the illuminating section is inserted into the body cavity of the biological organism, in which the fluorescent probe whose fluorescence characteristic changes by reacting with a molecule existing in the ACF or the fluorescent probe whose fluorescence characteristic changes by reacting with a product produced by activation of the molecule is applied to the inner wall of the body cavity in advance, and the excitation light is emitted onto the inner wall of the body cavity. When the fluorescent probe is excited by the excitation light, strong fluorescence can be obtained from areas with an abundance of the molecule in the inner wall of the body cavity, that is, areas with ACF (aberrant crypt foci).

Consequently, the counting section counts the number of fluorescence generation sites generated from accumulation sites of the fluorescent probe on the basis of the fluorescence included in the image information acquired by the image acquisition section, thereby achieving an ability to readily count the number of ACF without overlooking the existence of ACF and thus achieving reduced observation time.

In this aspect, the aforementioned molecule may be at least one of cyclin-D1, cox-2, β-catenin, iNOS, CD44, EGFR, Fzd1, and GST-π.

In the above aspect, the fluorescence observation apparatus may further include moving mechanism configured to move the illuminating section and the image acquisition section relative to the inner wall of the body cavity.

With this configuration, the image information can be acquired over a wide area along the inner wall of the body cavity while performing observation.

In the above aspect, the fluorescence observation apparatus may further include a fluorescent-probe discharging section that applies the fluorescent probes to the inner wall of the body cavity.

This configuration eliminates the need for an additional member for supplying the fluorescent probe to the biological organism.

In the above aspect, the counting section may count the number of fluorescence generation sites existing in an area between 0.4 and 0.8 from the center of the image based on the image information acquired by the image acquisition section when the distance from the center to an edge of the image is defined as 1.0.

With this configuration, the effect of parallax and noise can be reduced, thereby preventing an ACF counting error.

In the above aspect, the fluorescence observation apparatus may further include a fluorescence-intensity measuring section that measures the fluorescence intensity at each fluorescence generation site, and a fluorescence-intensity classifying section that classifies the number of fluorescence generation sites counted by the counting section in accordance with the fluorescence intensity at each fluorescence generation site measured by the fluorescence-intensity measuring section.

With this configuration, the degree of malignancy of each ACF can be determined on the basis of the magnitude of the fluorescence intensity at the corresponding fluorescence generation site measured by the fluorescence-intensity measuring section. For example, if the fluorescence intensity is high, the degree of malignancy of the ACF is high. Therefore, by using the fluorescence-intensity classifying section to classify the number of fluorescence generation sites in accordance with the fluorescence intensity, the future risk for cancer development or the like can be evaluated.

In the above aspect, the fluorescence observation apparatus may further include a fluorescence-size measuring section that measures the size of each fluorescence generation site, and a fluorescence-size classifying section that classifies the number of fluorescence generation sites counted by the counting section in accordance with the size of each fluorescence generation site measured by the fluorescence-size measuring section.

With this configuration, the degree of malignancy of each ACF can be determined on the basis of the size of the corresponding fluorescence generation site measured by the fluorescence-size measuring section. Therefore, by using the fluorescence-size classifying section to classify the number of fluorescence generation sites in accordance with the size thereof, the future risk for cancer development or the like can be evaluated.

In the above aspect, the fluorescence observation apparatus may further include a fluorescence-pattern determining section that detects a pattern of each fluorescence generation site and determines whether or not the pattern matches a pattern of an ACF, and a correcting section that subtracts the number of fluorescence generation sites determined as not satisfying a pattern condition of the ACF by the fluorescence-pattern determining section from the number of fluorescence generation sites counted by the counting section.

With this configuration, bright spots, other than ACF, occurring due to noise or the like can be removed in accordance with the pattern of each fluorescence generation site detected by the fluorescence-pattern determining section, thereby allowing for more accurate detection of ACF. Therefore, by using the correcting section to correct the counted number of fluorescence generation sites so as to accurately ascertain the number of ACF, the future risk for cancer development or the like can be finely evaluated. Since an ACF has, for example, a pattern formed of a group of hollow annular sections with high brightness, the ACF pattern condition may be set, for example, on the basis of a ratio between bright areas and dark areas within the pattern of each fluorescence generation site.

In the above aspect, the fluorescence observation apparatus may further include an image generating section that generates a two-dimensional image of the fluorescence generation sites counted by the counting section, and a pattern classifying section that classifies each fluorescence generation site in accordance with a pattern thereof on the basis of the two-dimensional image generated by the image generating section.

With this configuration, the degree of malignancy of each ACF can be determined on the basis of the pattern of the corresponding fluorescence generation site in the two-dimensional image generated by the image generating section, and the pattern classifying section can be used for the classification, thereby effectively using it for a diagnostic examination.

In the above aspect, the illuminating section may emit reference excitation light having a wavelength characteristic different from that of the excitation light, and the fluorescence observation apparatus may further include an image generating section that generates a two-dimensional fluorescence image and a two-dimensional reference fluorescence image on the basis of the image information corresponding to the excitation light and image information corresponding to the reference excitation light that are acquired by the image acquisition section, and that corrects the fluorescence image acquired using the excitation light by using the reference fluorescence image acquired using the reference excitation light.

With this configuration, since the fluorescence image acquired using the excitation light has fluorescence generation sites, generated by the excitation of the fluorescent probe, and noise, and the reference fluorescence image acquired using the reference excitation light only has noise, the image generating section can remove the noise from the fluorescence image so that the counting section can accurately count the number of ACF. The correction performed by the image generating section may be subtraction processing or division processing.

In the above aspect, the fluorescence observation apparatus may further include an image combining section that obtains a composite image by combining multiple sets of image information acquired by the image acquisition section while moving the image acquisition section using the moving mechanism, and the counting section may count the number of fluorescence generation sites with predetermined brightness or higher within the composite image obtained by the image combining section.

With this configuration, based on the composite image obtained by the image combining section, the number of ACF with a particularly high degree of malignancy can be ascertained in correspondence with the positions and the sizes thereof.

In the above aspect, the fluorescence observation apparatus may further include a reference line that is provided within the image information acquired by the image acquisition section and that moves together with the image acquisition section, and when the image acquisition section is moved by the moving mechanism, the counting section may count the number of fluorescence generation sites that cross over the reference line within the image information acquired by the image acquisition section.

By using the counting section to count the number of fluorescence generation sites every time a fluorescence generation site crosses over the reference line, the number and the positions of the ACF can be ascertained while the image acquisition section acquires the image of the inner wall of the body cavity, thereby achieving reduced observation time.

ADVANTAGEOUS EFFECTS OF INVENTION

The present invention advantageously reduces the load on a patient and facilitates identification of an examined site in an a posteriori manner.

BRIEF DESCRIPTION OF DRAWINGS

FIG. 3A illustrates a wavelength characteristic of illumination light.

FIG. 3B illustrates a wavelength characteristic of excitation light.

FIG. 3C illustrates a transmittance characteristic of an excitation-light cut filter.

FIG. 3D illustrates a wavelength characteristic of fluorescence from GST-$\pi$-sensitive fluorescent probes.

FIG. 4 is a flow chart illustrating the operation of the fluorescence observation apparatus in FIG. 1.

DESCRIPTION OF EMBODIMENTS

First Embodiment

A fluorescence observation apparatus according to a first embodiment of the present invention will be described below with reference to the drawings.

Figure 1:
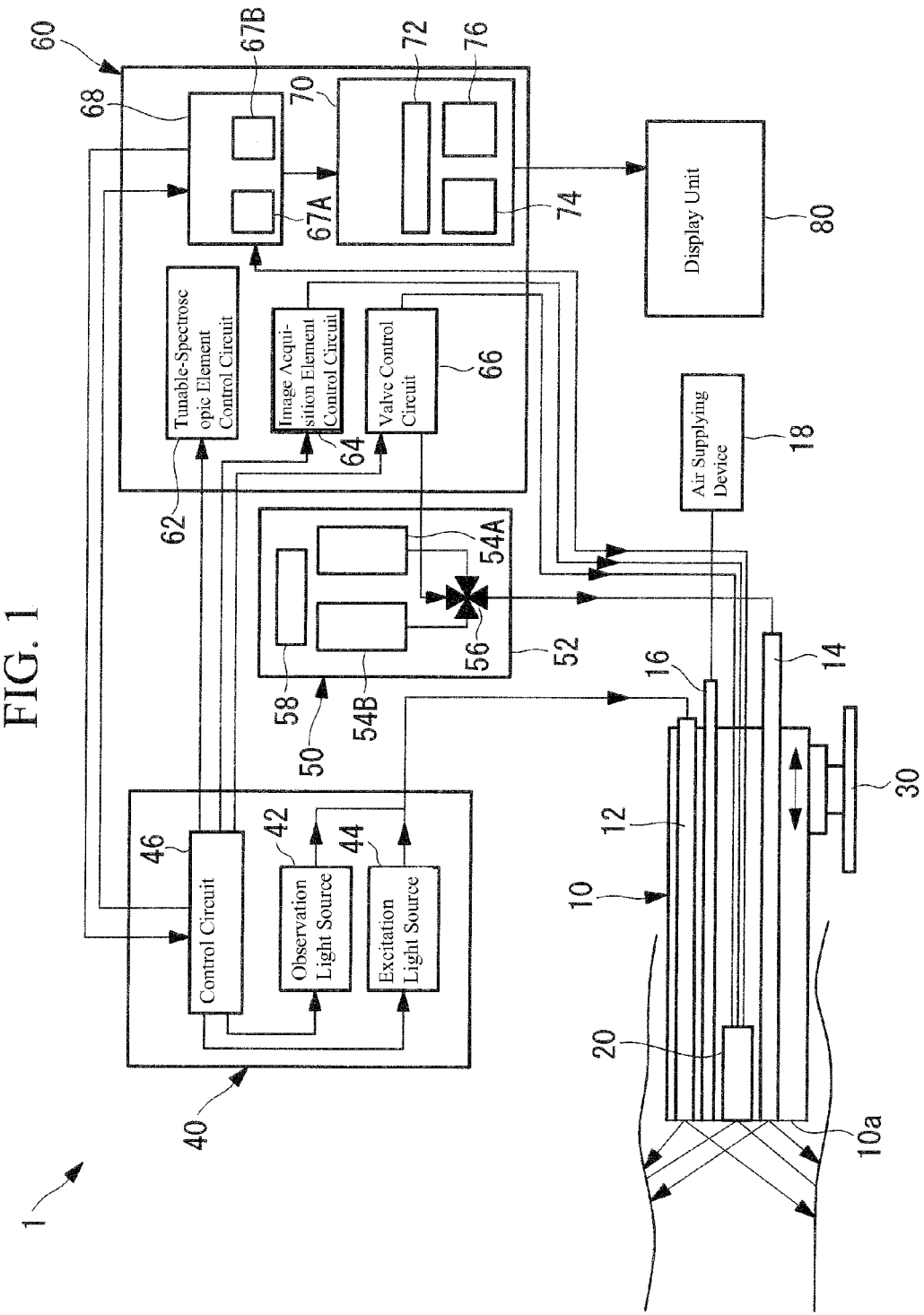
FIG. 1 is a schematic configuration diagram of a fluorescence observation apparatus according to a first embodiment of the present invention.

As shown in FIG. 1, a fluorescence observations apparatus 1 according to this embodiment is an endoscopic device and includes an insertion section 10 to be inserted into a body cavity of a biological organism and having an image acquisition unit (image acquisition section) 20 that acquires image information, a position control unit (moving mechanism) 30 that controls the position of the insertion section 10 within the body cavity, a light source unit (illuminating section) 40 that generates illumination light and excitation light to be emitted from a tip 10a of the insertion section 10, a liquid supplying unit 50 that supplies a fluorescent probe solution and a cleaning liquid to be ejected from the tip 10a of the insertion section 10, an overall control unit 60 that controls these units 20, 30, 40, and 50, and a display unit 80 that displays the image acquired by the image acquisition unit 20.

The insertion section 10 has an extremely narrow dimension so that it can be inserted into the body cavity of the biological organism. The insertion section 10 includes the image acquisition unit 20, a light guide 12 that transmits the illumination light and the excitation light received from the light source unit 40 to the tip 10a, and a liquid channel 14 and an air channel 16 that are formed through the insertion section 10 in the longitudinal direction. Reference numeral 18 denotes an air supplying device that sends air into the body cavity from the tip 10a via the air channel 16.

Figure 2:
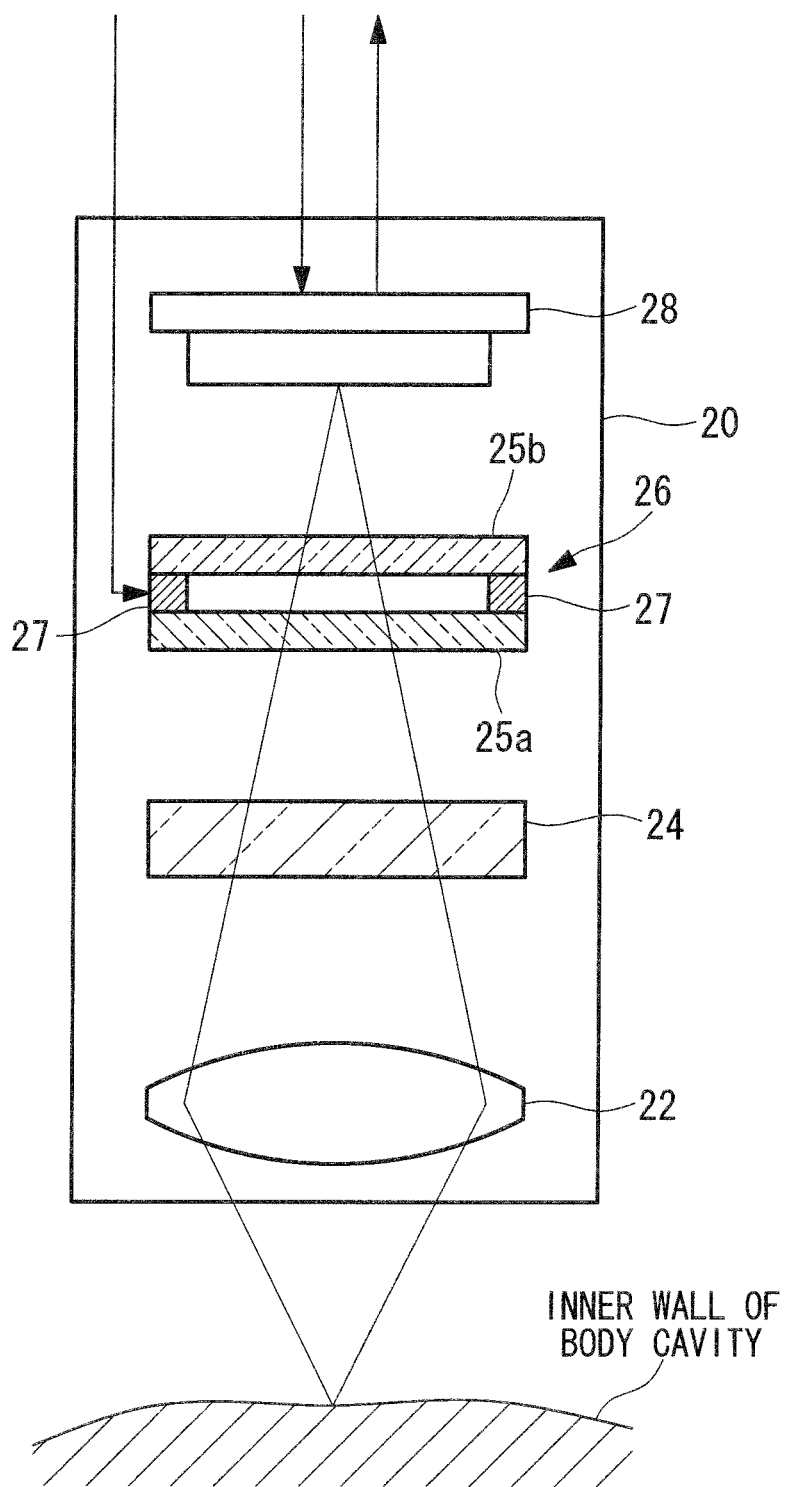
FIG. 2 is an enlarged schematic configuration diagram of an image acquisition unit in FIG. 1.

For example, as shown in FIG. 2, the image acquisition unit 20 includes an image-acquisition optical system 22 that collects return light or fluorescence received from an inner wall of the body cavity acting as a target, an excitation-light cut filter 24 that cuts excitation light received from the target via the image-acquisition optical system 22, a tunable spectroscopic element 26 whose spectral characteristics can be varied by the operation of the overall control unit 60, and an image acquisition element 28 that acquires an image of the return light or the fluorescence collected by the image-acquisition optical system 22 so as to acquire image information.

The tunable spectroscopic element 26 is, for example, an etalon optical filter equipped with two flat optical members 25a and 25b arranged in parallel with a certain distance therebetween and provided with reflective films on opposing surfaces thereof, and an actuator 27 that changes the distance between these optical members 25a and 25b. The tunable spectroscopic element 26 can vary the spectral characteristics, that is, the wavelength range of light to be transmitted therethrough, by changing the distance between the optical members 25a and 25b by the operation of the actuator 27.

The actuator 27 is, for example, a piezoelectric element.

The position control unit 30 is configured to move the insertion section 10 relative to the inner wall of the body cavity of the biological organism. Furthermore, the position control unit 30 includes, for example, a measuring section (not shown) that measures the position of the insertion section 10 within the body cavity by means of a magnetic field, X-rays, or the like.

The light source unit 40 includes a white-light-observation light source 42 that illuminates the inner wall of the body cavity and emits blue, green, and red illumination light rays for acquiring a white-light image, a fluorescence-excitation light source 44 that emits excitation light onto the inner wall within the body cavity so as to excite a fluorescent material existing within the inner wall of the body cavity, thus generating fluorescence, and a light-source control circuit 46 that controls the white-light-observation light source 42 and the fluorescence-excitation light source 44.

The fluorescence-excitation light source 44 is, for example, an argon laser (or a semiconductor laser). An LED (light-emitting diode) or a combination of a xenon lamp and a specific-wavelength-transmission filter may be used as the fluorescence-excitation light source 44.

For example, the illumination light to be emitted from the white-light-observation light source 42 has the wavelength characteristic shown in FIG. 3A, whereas the excitation light to be emitted from the fluorescence-excitation light source 44 has the wavelength characteristic shown in FIG. 3B. The excitation-light cut filter 24 has the transmittance characteristic shown in FIG. 3C. The fluorescence from GST-π-sensitive fluorescent probes generated at the inner wall of the body cavity has, for example, the wavelength characteristic shown in FIG. 3D.

The light-source control circuit 46 actuates the white-light-observation light source 42 and the fluorescence-excitation light source 44 by switching between them at a predetermined timing.

The liquid supplying unit 50 includes a thermostatic bath 52, a fluorescence tank 54A and a cleaning tank 54B that are disposed within the thermostatic bath 52 and that respectively store the fluorescent probe solution and the cleaning liquid, and a valve 56 that feeds/blocks the liquids from the fluorescence tank 54A and the cleaning tank 54B. Reference numeral 58 denotes a temperature display section that displays the temperature of the thermostatic bath 52.

The thermostatic bath 52 can maintain the liquids in the fluorescence tank 54A and the cleaning tank 54B at a constant temperature.

The valve 56 switches between the fluorescence tank 54A and the cleaning tank 54B so as to connect one of the tanks to the liquid channel 14 of the insertion section 10 in a flowable manner.

For example, a solution in which enzyme-sensitive fluorescent probes are dissolved, specifically, a solution in which GST-π-sensitive fluorescent probes are dissolved, is used as the fluorescent probe solution. The GST-π-sensitive fluorescent probes hardly generate fluorescence prior to reacting with GSH (glutathione), but have properties by which they change to a material that emits strong fluorescence by reacting with GSH via GST-π existing in an organ within the body cavity.

An ACF is known to have an abundance of GST-π occurring therein. When excitation light is emitted onto the inner wall of the body cavity coated with the fluorescent probe solution in which the GST-π-sensitive fluorescent probes are dissolved, the GST-π-sensitive fluorescent probes reacting with GSH via GST-π occurring in the inner wall of the body cavity are excited, whereby strong fluorescence can be obtained from areas where GST-π exists abundantly, that is, areas where ACF exist.

The overall control unit 60 includes a tunable-spectroscopic-element control circuit 62 that controls the spectral characteristics of the tunable spectroscopic element 26, an image-acquisition-element control circuit 64 that drives and controls the image acquisition element 28, a valve control circuit 66 that controls the opening and the closing of the valve 56 within the liquid supplying unit 50, a frame memory 68 that stores the image information acquired by the image acquisition element 28, and an image-processing and determination device 70 that processes the image information stored in the frame memory 68.

The frame memory 68 includes a white-light-image memory 67A that stores image information (referred to as "white-light image information" hereinafter) acquired by the image acquisition element 28 by taking an image of return light, and a fluorescence-image memory 67B that stores image information (referred to as "fluorescence image information" hereinafter) acquired by the image acquisition element 28 by taking an image of fluorescence. In the fluorescence-image memory 67B, the fluorescence image information may be stored in correspondence with the positional information of the insertion section 10 measured by the position control unit 30.

The tunable-spectroscopic-element control circuit 62 and the image-acquisition-element control circuit 64 are connected with the light-source control circuit 46 of the light source unit 40, and the tunable spectroscopic element 26 and the image acquisition element 28 are driven and controlled in synchronization with the timing at which the light-source control circuit 46 switches between the white-light-observation light source 42 and the fluorescence-excitation light source 44.

Specifically, when R, G, and B illumination light rays are sequentially emitted from the white-light-observation light source 42 by the operation of the light-source control circuit 46, that is, when performing white-light observation based on an RGB frame-sequential method, the spectral characteristics of the tunable spectroscopic element 26 are changed by the operation of the tunable-spectroscopic-element control circuit 62 to spectral characteristics for selectively transmitting the return light. Furthermore, the image-acquisition element 28 is controlled by the operation of the image-acquisition-element control circuit 64 so as to acquire an image of the return light transmitted through the tunable spectroscopic element 26 and to output the acquired white-light image information to the white-light-image memory 67A.

On the other hand, when the excitation light is emitted from the fluorescence-excitation light source 44 by the operation of the light-source control circuit 46, that is, when performing fluorescence observation, the spectral characteristics of the tunable spectroscopic element 26 are changed by the operation of the tunable-spectroscopic-element control circuit 62 to spectral characteristics for selectively transmitting the fluorescence. Furthermore, the image acquisition element 28 is controlled by the operation of the image-acquisition-element control circuit 64 so as to acquire an image of the fluorescence transmitted through the tunable spectroscopic element 26 and to output the acquired fluorescence image information to the fluorescence-image memory 67B.

When performing fluorescence observation, the valve control circuit 66 controls the opening and the closing of the valve 56 so as to spray the fluorescent probe solution stored in the fluorescence tank 54A. Furthermore, before spraying the fluorescent probe solution and before performing fluorescence observation after the spraying of the fluorescent probe solution, the valve control circuit 66 controls the opening and the closing of the valve 56 so as to clean the inner wall surface of the body cavity of the biological organism or to spray the cleaning liquid for removing the fluorescent probes accumulated on the inner wall surface of the body cavity.

In the case of white-light observation, the image-processing and determination device 70 receives the white-light image information, acquired as a result of the emission of the illumination light, from the white-light-image memory 67A and makes the display unit 80 display the white-light image. On the other hand, in the case of fluorescence observation, the image-processing and determination device 70 receives the fluorescence image information, acquired as a result of the emission of the excitation light, from the fluorescence-image memory 67B and makes the display unit 80 display the fluorescence image.

While the fluorescence image is displayed on the display unit 80, the image-processing and determination device 70 sets a reference line (not shown) that moves together with the image acquisition element 28. The reference line is, for example, an annular line having a predetermined size and centered on the center of the image.

The image-processing and determination device 70 is provided with a counting section 72 that counts the number of fluorescence generation sites included in the fluorescence image information, a fluorescence-intensity measuring section 74 that measures the fluorescence intensity at each fluorescence generation site, and a fluorescence-intensity classifying section 76 that classifies the number of fluorescence generation sites counted by the counting section 72 in accordance with the fluorescence intensity at each fluorescence generation site measured by the fluorescence-intensity measuring section 74.

The counting section 72 is for counting the number of fluorescence generation sites (bright spots) generated from accumulation sites of the GST-π-sensitive fluorescent probes, specifically, the number of ACF. An ACF has, for example, a pattern formed of a group of hollow annular sections with high brightness. The number of ACF counted by the counting section 72, the fluorescence intensity of each ACF measured by the fluorescence-intensity measuring section 74, the classification result of the ACF obtained by the fluorescence-intensity classifying section 76, and the like are displayed on the display unit 80.

The operation of the fluorescence observation apparatus 1 according to this embodiment having the above-described configuration will now be described with reference to a flow chart in FIG. 4.

For example, when observing the inner wall of the body cavity in the rectum of the biological organism acting as a target by using the fluorescence observation apparatus 1 according to this embodiment, the inside of the rectum is cleaned in a pre-treatment, and the insertion section 10 is subsequently inserted into the rectum until the tip 10a faces the inner wall of the body cavity acting as the target.

At this time, for example, the air supplying device 18 is actuated so as to send air into the body cavity via the air channel 16, causing the rectum to expand. Furthermore, it is preferable that the position control unit 30 be actuated so as to dispose the insertion section 10 on a central axis in the cross section of the rectum. With this disposition, the observation distance from the image acquisition element 28 to the surrounding inner wall of the body cavity can be maintained in a substantially uniform state.

In this state, the light source unit 40 and the overall control unit 60 are actuated. By the operation of the light-source control circuit 46, the white-light-observation light source 42 is actuated and thus generates illumination light, whereby white-light observation is performed (step S1). The illumination light emitted from the white-light-observation light source 42 is transmitted to the tip 10a of the insertion section 10 via the light guide 12 so as to be emitted onto the target. The emitted illumination light is reflected at the surface of the target, and the return light thereof is collected by the image-acquisition optical system 22.

The return light collected by the image-acquisition optical system 22 is transmitted through the excitation-light cut filter 24 before becoming incident on the tunable spectroscopic element 26. In this case, the tunable spectroscopic element 26 is controlled by the operation of the tunable-spectroscopic-element control circuit 62 so as to be set in a mode for selectively transmitting the return light. Consequently, the return light is entirely transmitted through the tunable spectroscopic element 26.

Based on the operation of the image-acquisition-element control circuit 64, the image acquisition element 28 acquires an image of the return light transmitted through the tunable spectroscopic element 26, thereby acquiring white-light image information. The white-light image information acquired by the image acquisition element 28 is stored in the white-light-image memory 67A and is sent to the display unit 80 by the image-processing and determination device 70 so as to be displayed thereon.

When performing fluorescence observation by using the fluorescent probes, the valve 56 is opened by the operation of the valve control circuit 66, whereby the cleaning tank 54B and the liquid channel 14 are connected to each other. Consequently, the cleaning liquid is sprayed into the rectum of the biological organism, thereby washing off a residue (a deposit such as feces) existing on the inner wall surface of the body cavity (step S2).

After the spraying of the cleaning liquid, the cleaning tank 54B is switched to the fluorescence tank 54A by the operation of the valve control circuit 66, thereby connecting the fluorescence tank 54A and the liquid channel 14 to each other and thus spraying the fluorescent probe solution into the rectum (step S3).

After a predetermined time period has elapsed since the spraying of the fluorescent probe solution, the cleaning tank 54B and the liquid channel 14 are connected to each other again by the operation of the valve control circuit 66, thereby spraying the cleaning liquid into the rectum and thus removing the fluorescent probe solution existing on the inner wall surface of the body cavity (step S4).

After the cleaning process, the operation of the light-source control circuit 46 causes switching from the white-light-observation light source 42 to the fluorescence-excitation light source 44 from which excitation light is emitted, thereby performing fluorescence observation (step S5). The excitation light emitted from the fluorescence-excitation light source 44 is transmitted to the tip 10a of the insertion section 10 via the light guide 12 so as to be emitted onto the target. Thus, the fluorescent probes penetrated in the inner wall of the body cavity acting as the target are excited, whereby fluorescence is emitted.

The fluorescence emitted from the target is collected by the image-acquisition optical system 22 of the image acquisition unit 20 and is transmitted through the excitation-light cut filter 24 before becoming incident on the tunable spectroscopic element 26. In this case, the tunable spectroscopic element 26 is controlled by the operation of the tunable-spectroscopic-element control circuit 62 so as to be switched to a mode for selectively transmitting the fluorescence. Thus, the incident fluorescence is transmitted through the tunable spectroscopic element 26.

Based on the operation of the image-acquisition-element control circuit 64, the image acquisition element 28 acquires an image of the fluorescence transmitted through the tunable spectroscopic element 26, thereby acquiring fluorescence image information. The fluorescence image information acquired by the image acquisition element 28 is stored in the fluorescence-image memory 67B and is sent to the display unit 80 by the image-processing and determination device 70 so as to be displayed thereon.

In the image-processing and determination device 70, the counting section 72 is actuated so as to count the number of fluorescence generation sites included in the fluorescence image information, that is, the number of ACF (step S6). In this case, the insertion section 10 is moved by the position control unit 30 so that the fluorescence image information is acquired over a wide area along the inner wall of the body cavity.

Figure 5:
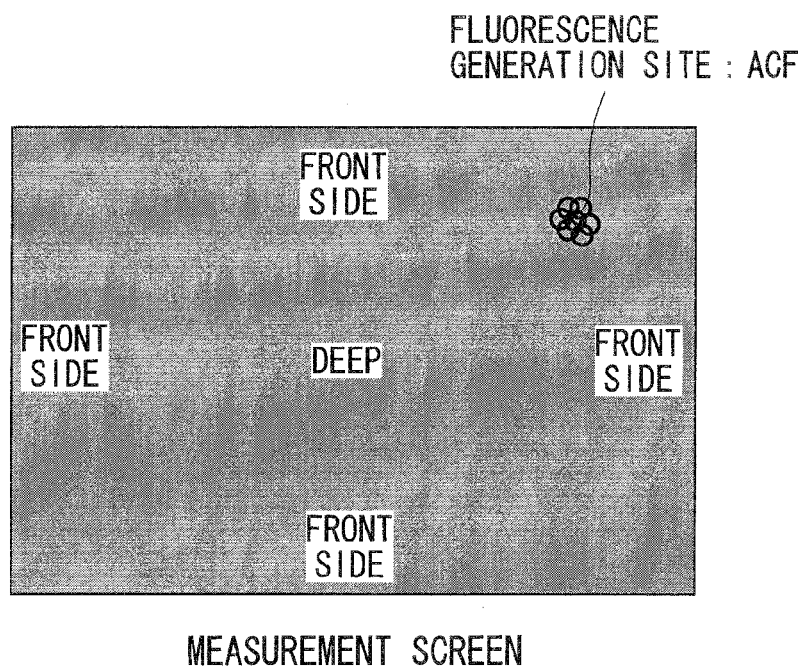
FIG. 5 is a diagram illustrating an image displayed on a display unit in FIG. 1.

As the insertion section 10 inserted in the rectum is pulled while performing fluorescence observation, that is, as image acquisition is performed while moving the tip 10a away from the deeper side of the rectum with the base end of the insertion section 10 serving as the front side in the moving direction, an image of the target is displayed on the display unit 80 as if it were moving from the outer side of the image to the inner side, as shown in FIG. 5.

In the counting section 72, when a bright spot (ACF) appearing from the outer side of the image moves toward the inner side of the image and crosses over the annular reference line (in other words, when the bright spot (ACF) enters a predetermined region of the image), the number of bright spots (ACF) that have crossed over the reference line is counted. By performing the counting process in this manner, the number and the positions of the ACF can be readily ascertained while the image acquisition element 28 acquires the image of the inner wall of the body cavity.

With the fluorescence observation apparatus 1 according to this embodiment, the excitation light is emitted onto the inner wall, coated with the GST-π-sensitive fluorescent probe solution, of the body cavity of the biological organism so that the GST-π-sensitive fluorescent probes reacting with GSH via GST-π occurring in the inner wall of the body cavity are excited, whereby strong fluorescence can be obtained from areas where GST-π exists abundantly, that is, areas where ACF exist. Therefore, the counting section 72 can readily and accurately count the number of ACF without miscounting the number of bright spots due to noise or the like or overlooking the existence of ACF.

Figure 6:
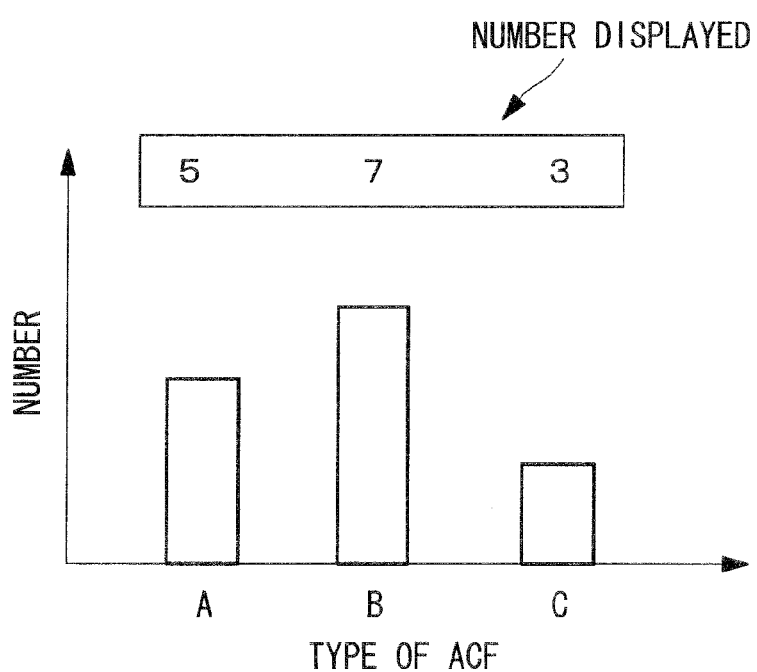
FIG. 6 is a diagram illustrating a graph in which the number of ACF is classified in accordance with the fluorescence intensity by a fluorescence-intensity classifying section in FIG. 1.

Subsequently, the fluorescence-intensity measuring section 74 measures the fluorescence intensity of the ACF, the number of which has been counted by the counting section 72, and the fluorescence-intensity classifying section 76 classifies the number of ACF in accordance with the fluorescence intensity of each ACF measured by the fluorescence-intensity measuring section 74. For example, FIG. 6 shows an example of a graph in a case where the inner wall of the body cavity acting as the target has five ACF with a fluorescence intensity A, seven ACF with a fluorescence intensity B, and three ACF with a fluorescence intensity C.

The degree of malignancy of each ACF can be determined on the basis of the magnitude of the fluorescence intensity of the ACF measured by the fluorescence-intensity measuring section 74. For example, if the fluorescence intensity is high, the degree of malignancy of the ACF is high. By classifying the number of ACF in accordance with the fluorescence intensity in this manner, the future risk for cancer development or the like can be evaluated.

When the entire observation is completed after the ACF classification, the number of the ACF and the like are displayed on the display unit 80 (step S7).

As described above, with the fluorescence observation apparatus 1 according to this embodiment, fluorescence observation is performed over a wide area along the inner wall of the body cavity while moving the insertion section 10, by using the fluorescent probes that react with GSH via GST-π abundantly occurring in the ACF, so that the number of ACF can be readily and accurately counted without overlooking the existence of ACF, thereby achieving reduced observation time. Furthermore, by classifying the counted number of ACF in accordance with the fluorescence intensity, the future risk for cancer development or the like can be evaluated.

Although the fluorescence intensity at each fluorescence generation site is measured by the fluorescence-intensity measuring section 74 and the number of fluorescence generation sites is classified in accordance with the fluorescence intensity by the fluorescence-intensity classifying section 76 in this embodiment, the image-processing and determination device 70, for example, may alternatively include an image generating section, in place of the fluorescence-intensity measuring section 74, for generating a two-dimensional fluorescence image of bright spots, the number of which is counted by the counting section 72, and a pattern classifying section, in place of the fluorescence-intensity classifying section 76, for classifying the bright spots generated by the image generating section in accordance with the pattern thereof.

In this case, the image generating section may generate the fluorescence image on the basis of the fluorescence image information sent from the fluorescence-image memory 67B and make the display unit 80 display the generated fluorescence image. Furthermore, the counting section 72 may be configured to count not only the number of bright spots but also the number of bright spots classified in accordance with the pattern thereof. Moreover, upon completion of the observation, the pattern of each of the bright spots may be displayed on a screen, an operator may then classify each bright spot in accordance with the pattern thereof, and the classified result may be displayed on the screen in the form of a graph or the like.

Figure 7C:
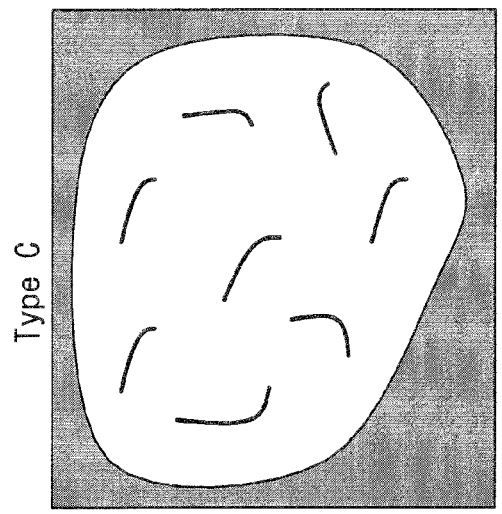
FIG. 7C illustrates the structure of an ACF with a collapsed pit pattern.
Figure 7B:
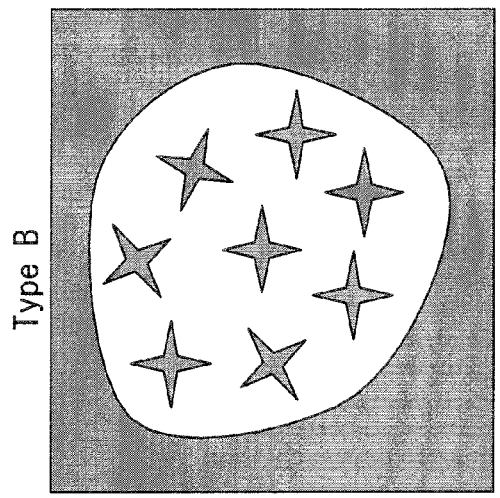
FIG. 7B illustrates the structure of an ACF with a starfish-like pit pattern.
Figure 7A:
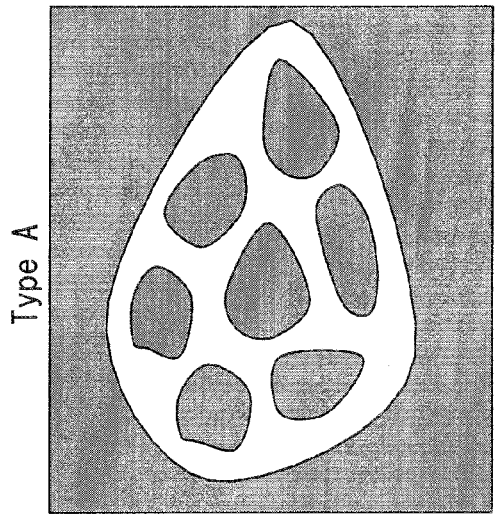
FIG. 7A illustrates the structure of an ACF with a circular pit pattern.

It is known that the degree of malignancy of an ACF relates to its structure. Examples of structures of ACF include type A in which the pit pattern is circular (a near-circular pattern), as shown in FIG. 7A, type B in which the pit pattern is starfish-like (a near-cross-shaped pattern), as shown in FIG. 7B, and type C in which the pit pattern is collapsed (a near-linear pattern), as shown in FIG. 7C. The degree of malignancy increases in the following order: type A<type B<type C.

In this embodiment, although white-light observation is performed by using the white-light-observation light source 42, and the cleaning liquid and the fluorescent probe solution are sprayed by using the liquid supplying unit 50, the white-light-observation light source 42 and the liquid supplying unit 50 may alternatively be omitted, and the cleaning liquid and the fluorescent probe solution may be applied in a pre-treatment prior to performing fluorescence observation by using an alternative member.

Figure 8:
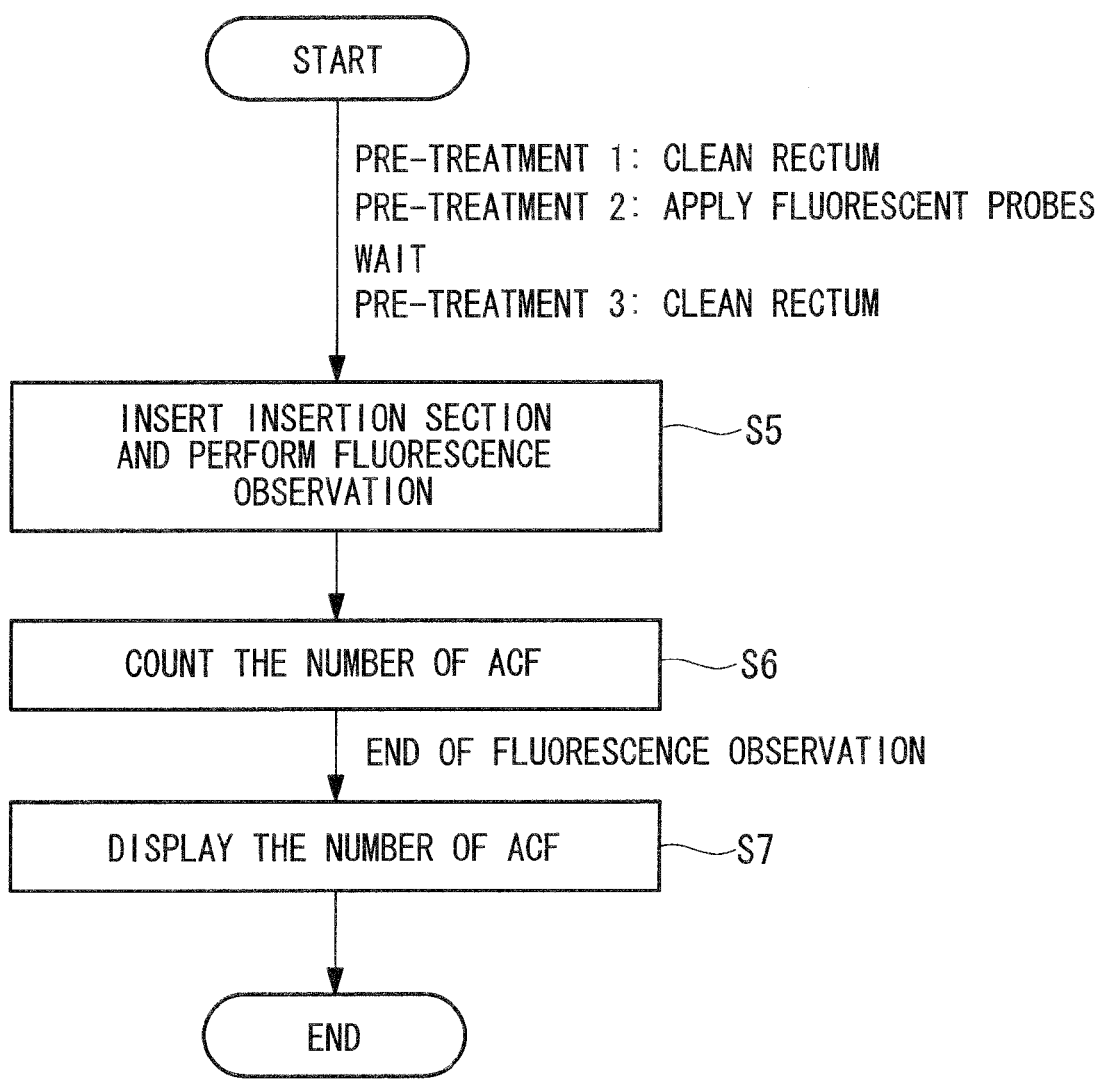
FIG. 8 is a flow chart illustrating the operation of a fluorescence observation apparatus with an alternative configuration according to the first embodiment of the present invention.

In this case, for example, as shown in a flow chart in FIG. 8, after cleaning the rectum using the alternative member (pre-treatment 1), spraying the fluorescent probe solution (pre-treatment 2), and then removing the fluorescent probe solution (pre-treatment 3) as pre-treatment steps, the insertion section 10 may be inserted into the body cavity to perform fluorescence observation (step S5), the number of ACF may be counted (step S6), and the number of ACF may be displayed (step S7).

Furthermore, in this embodiment, for example, a transparent cover that covers the periphery of the insertion section 10 may be provided. In this case, the cover may be fixed to the inner wall of the body cavity inside the rectum so as to maintain the shape of the rectum, and only the insertion section 10 may be moved by the position control unit 30. By using the cover to maintain the shape of the rectum so that no creases or the like are formed in the inner wall of the body cavity, the number of ACF can be accurately counted more readily. It is preferable that the cover be of a disposable type. A balloon-type cover may be used.

Furthermore, for example, the insertion section 10 may be made bendable in a direction orthogonal to the longitudinal direction thereof, so that when a bright spot, such as a fluorescence generation site, is found, the insertion section 10 may be bent so as to set the tip 10a to face the bright spot, thereby performing magnified observation.

Figure 9:
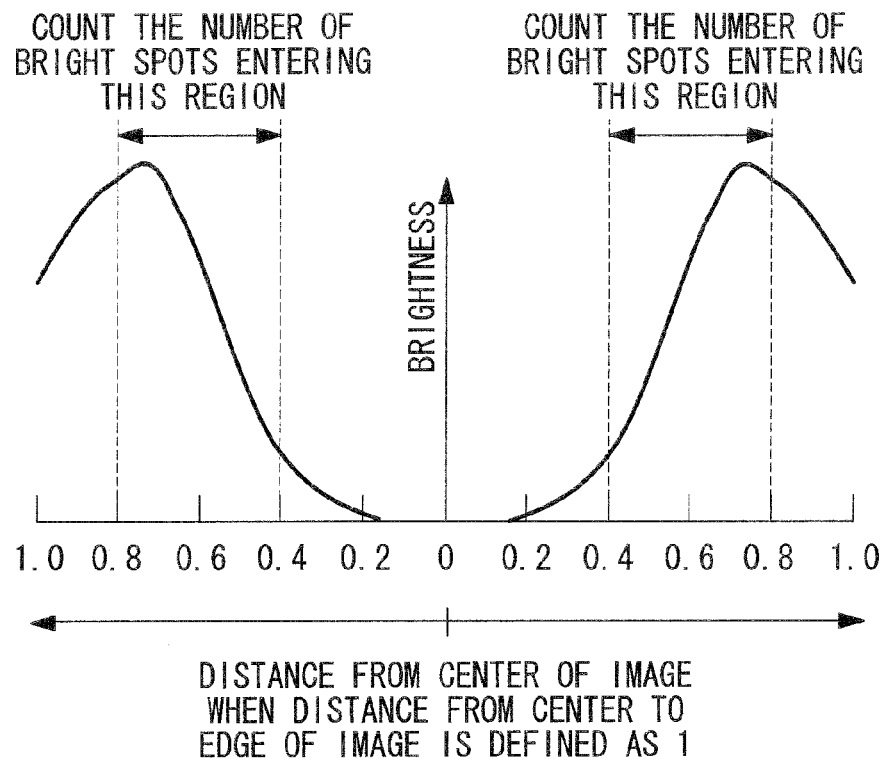
FIG. 9 is a diagram illustrating the relationship between the distance from the center of an image and the brightness thereof when the distance from the center to an edge of the image is defined as 1.
Figure 10:
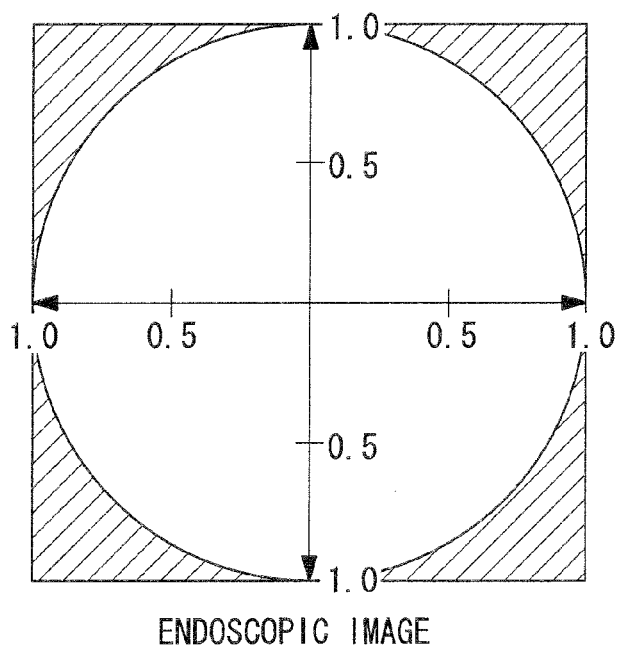
FIG. 10 is a diagram illustrating an image acquired by the fluorescence observation apparatus in FIG. 1.

The brightness distribution of an image when taken inside a tube (such as a rectum) is, for example, as shown in FIG. 9. In the figure, the ordinate denotes the brightness, whereas the abscissa denotes the distance from the center of the image when the distance from the center to an edge of the image is defined as 1. In FIGS. 9 and 10, an image position between 0.8 and 1.0 (i.e., a position far from the center of the image but close to the edge of the image) is susceptible to the structure inside the tube and is in a range where it is difficult to obtain a stable fluorescence signal due to the effect of positional deviation (parallax) between the illuminating position of the tip 10a of the insertion section 10 and the observation optical system. Therefore, counting the number of bright spots when they are positioned between 0.8 and 1.0 results in a large amount of error. On the other hand, a position between 0 and 0.4 (i.e., a position close to the center of the image) provides a weak fluorescence signal and is susceptible to noise since the distance from the tip 10a of the insertion section 10 is far. Therefore, it is preferable to count the number of bright spots when they exist in an area between 0.4 and 0.8.

This embodiment can be modified as follows.

Although each ACF is classified in accordance with the fluorescence intensity by the fluorescence-intensity measuring section 74 and the fluorescence-intensity classifying section 76 in this embodiment, a first modification in which, for example, a fluorescence-size measuring section that measures the size of a fluorescence generation site is used in place of the fluorescence-intensity measuring section 74 and a fluorescence-size classifying section that classifies the number of fluorescence generation sites counted by the counting section 72 in accordance with the size of each fluorescence generation site measured by the fluorescence-size measuring section is used in place of the fluorescence-intensity classifying section 76 is permissible. Since the degree of malignancy of each ACF can be determined in accordance with the size of the ACF, and the number of ACF is classified in accordance with the size thereof, the future risk for cancer development or the like can be evaluated.

As a second modification, for example, a fluorescence-pattern determining section that detects the pattern of a fluorescence generation site and determines whether or not the pattern matches an ACF pattern may be used in place of the fluorescence-intensity measuring section 74, and a correcting section that subtracts the number of fluorescence generation sites determined as not satisfying the ACF pattern condition by the fluorescence-pattern determining section from the number of fluorescence generation sites counted by the counting section 72 may be used in place of the fluorescence-intensity classifying section 76.

Thus, bright spots, other than ACF, occurring from noise or the like can be removed in accordance with the pattern of each fluorescence generation site, thereby allowing for more accurate detection of ACF. Consequently, by correcting the counted number of fluorescence generation sites so as to accurately ascertain the number of ACF, the future risk for cancer development or the like can be finely evaluated. The ACF pattern condition may be set, for example, on the basis of a ratio between bright areas and dark areas within the pattern of each fluorescence generation site.

Although the image-processing and determination device 70 sets the reference line in the image information and the counting section 72 counts the number of ACF that cross over the reference line in this embodiment, a third modification in which, for example, the image-processing and determination device 70 includes an image combining section that obtains a composite image by combining multiple sets of image information acquired while moving the insertion section 10, and the counting section 72 counts the number of fluorescence generation sites with predetermined brightness or higher within the composite image formed by the image combining section is permissible. Thus, based on the composite image obtained by the image combining section, the number of ACF with a particularly high degree of malignancy can be ascertained in correspondence with the positions and the sizes thereof in an a posteriori manner.

Second Embodiment

Figure 11:
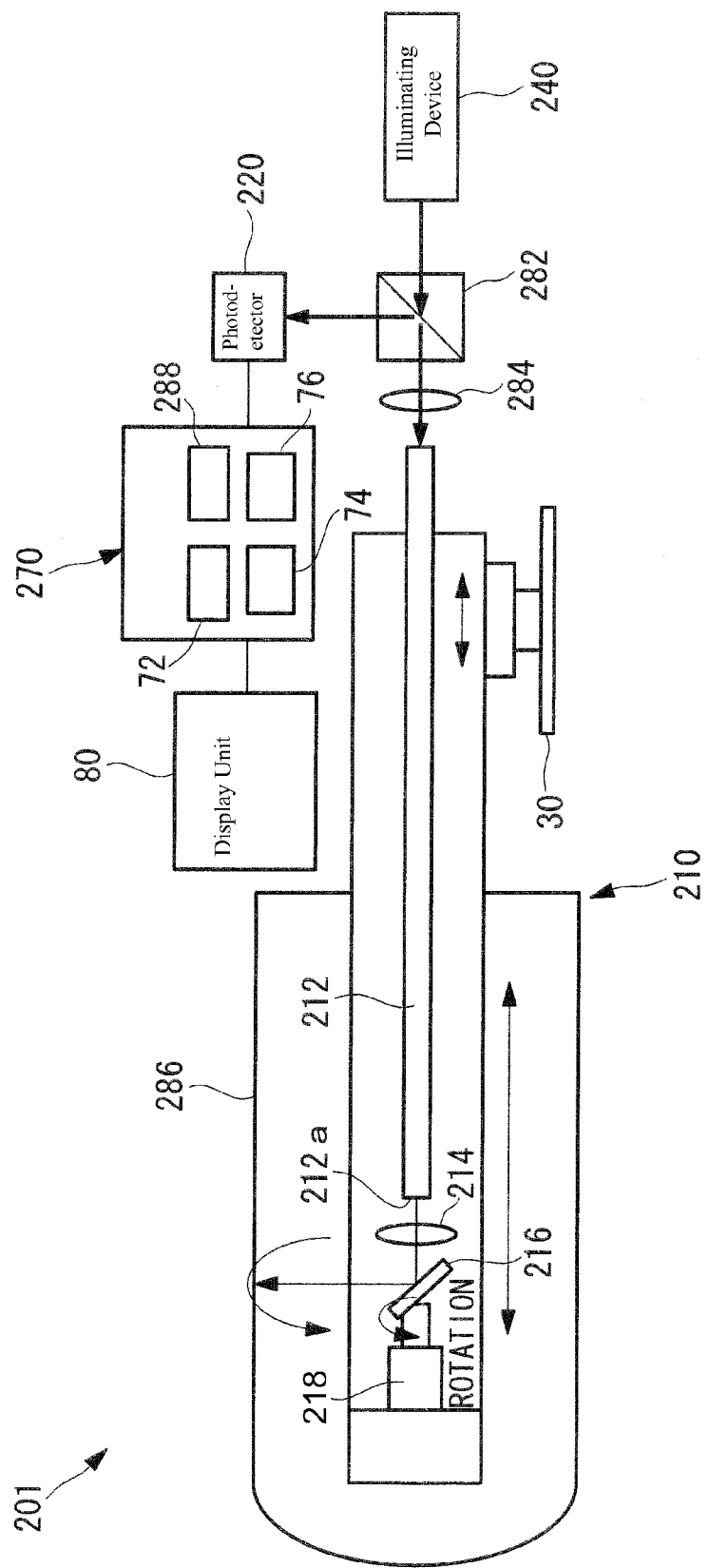
FIG. 11 is a schematic configuration diagram of a fluorescence observation apparatus according to a second embodiment of the present invention.

Next, a fluorescence observation apparatus according to a second embodiment of the present invention will be described with reference to FIG. 11.

A fluorescence observation apparatus 201 according to this embodiment is a scanning-type fluorescence observation apparatus that scans an inner wall of a body cavity of a biological organism so as to acquire an image thereof. The fluorescence observation apparatus 201 includes an insertion section 210 that is to be inserted into the body cavity of the biological organism, an illuminating device (illuminating section) 240 that generates excitation light to be emitted from the insertion section 210, a beam splitter 282 that splits the excitation light emitted from the illuminating device 240 and fluorescence generated at the inner wall of the body cavity from each other, a PD (photodetector, image acquisition section) 220 that acquires an image of the fluorescence split by the beam splitter 282 so as to acquire fluorescence image information, and an image-information processing device 270 that processes the fluorescence image information acquired by the PD 220. Reference numeral 284 denotes a first collimator lens.

In the following description, sections with the same configurations as those in the fluorescence observation apparatus 1 according to the first embodiment are given the same reference numerals, and descriptions thereof will be omitted.

The insertion section 210 includes a transparent cover 286 that covers the periphery thereof, a fiber 212 that optically guides the excitation light received from the illuminating device 240 via the beam splitter 282 and the first collimator lens 284 and emits the excitation light from an emission end 212a, a second collimator lens 214, a reflective mirror 216 that reflects the excitation light transmitted through the second collimator lens 214 in a direction orthogonal to the light axis, and a rotating mechanism 218 that rotates the reflective mirror 216.

The image-information processing device 270 includes an image combining section 288 that obtains a composite image by combining multiple sets of fluorescence image information acquired by the PD 220, a counting section 72, a fluorescence-intensity measuring section 74, and a fluorescence-intensity classifying section 76.

Figure 12:
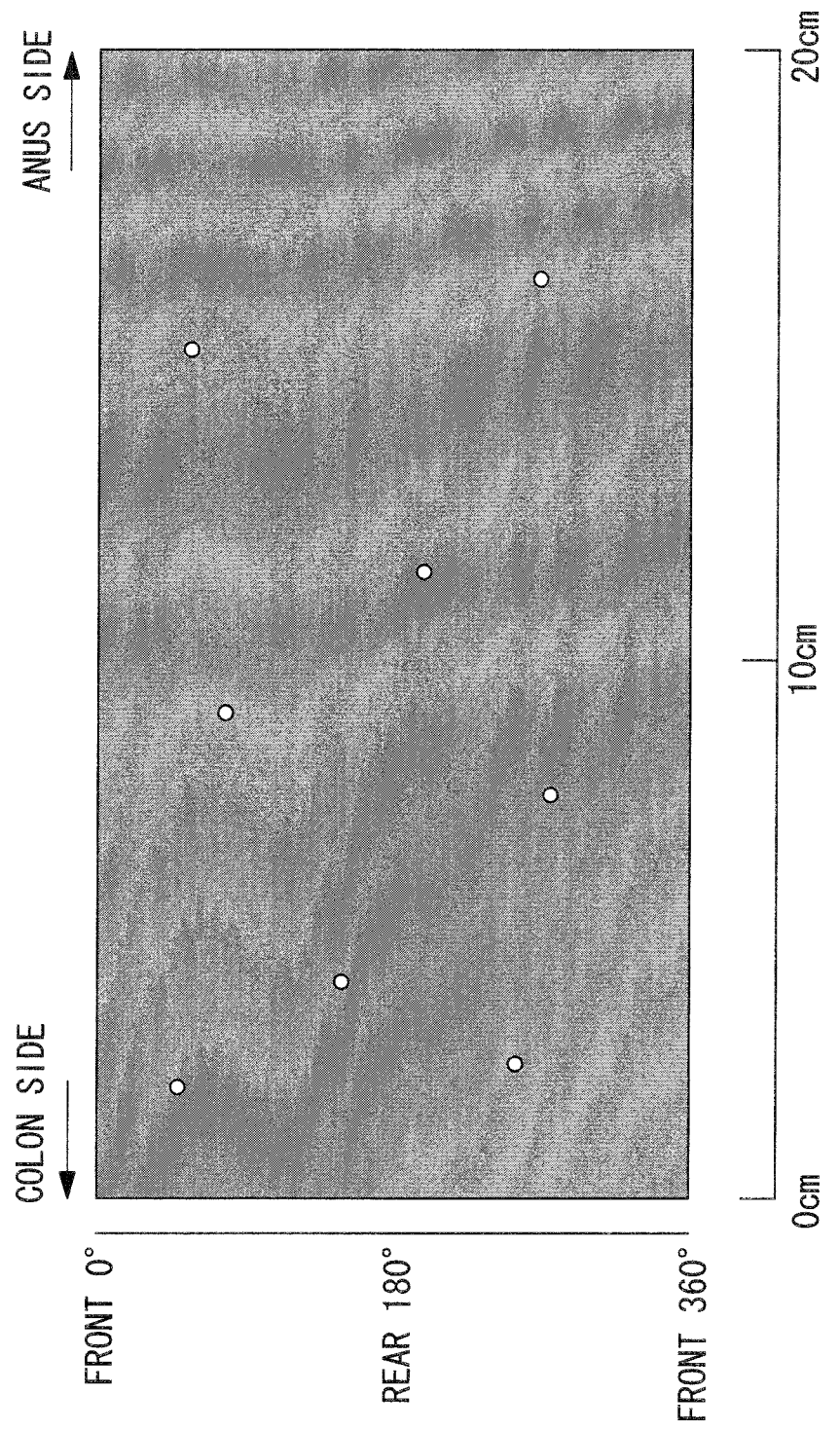
FIG. 12 is a diagram illustrating a composite image obtained by an image combining section in FIG. 11.

The image combining section 288 is configured to obtain the composite image of the entire inner wall of the body cavity of the rectum on the basis of the position of the insertion section 210 measured by the position control unit 30 and the rotational angle of the reflective mirror 216. The composite image obtained by the image combining section 288 is displayed on a display section 280 while being updated during fluorescence observation. The counting section 72 counts the number of ACF existing in the composite image after the fluorescence observation and displays it on the display section 280. The composite image may be such that, for example, as shown in FIG. 12, the ordinate thereof denotes the rotational angle of the reflective mirror 216 and the abscissa thereof denotes the position in the rectum in the longitudinal direction thereof from the colon side toward the anus side.

Regarding the fluorescence observation apparatus 201 having such a configuration, the insertion section 210 is inserted into the body cavity to which GST-π-sensitive fluorescent probes are applied in advance, and the excitation light emitted from the illuminating device 240 and transmitted through the beam splitter 282 is optically guided by the fiber 212 so as to be emitted from the emission end 212a. The excitation light emitted from the emission end 212a is reflected by the reflective mirror 216 that is rotated by the operation of the rotating mechanism 218, so as to be emitted in the circumferential direction from a side surface of the insertion section 210 onto the inner wall of the body cavity of the rectum. Then, fluorescence generated at the inner wall of the body cavity is reflected by the reflective mirror 216, is optically guided by the fiber 212, and is split by the beam splitter 282 before becoming incident on the PD 220. Thus, an image of the fluorescence incident on the PD 220 is acquired, whereby fluorescence image information is acquired.

As described above, with the fluorescence observation apparatus 201 according to this embodiment, fluorescence observation is performed by using the reflective mirror 216 and the rotating mechanism 218 to circumferentially scan the inner wall of the body cavity of the rectum and by using the position control unit 30 to move the insertion section 210 in the longitudinal direction thereof relative to the inner wall of the body cavity, whereby image information of the entire inner wall of the body cavity in the rectum can be acquired. Then, based on the composite image obtained by the image combining section 288, the number of ACF with a particularly high degree of malignancy can be ascertained in correspondence with the positions and the sizes thereof. Furthermore, since there is no need to dispose an image acquisition section within the insertion section 210, the configuration of the insertion section 210 can be simplified.

Figure 13:
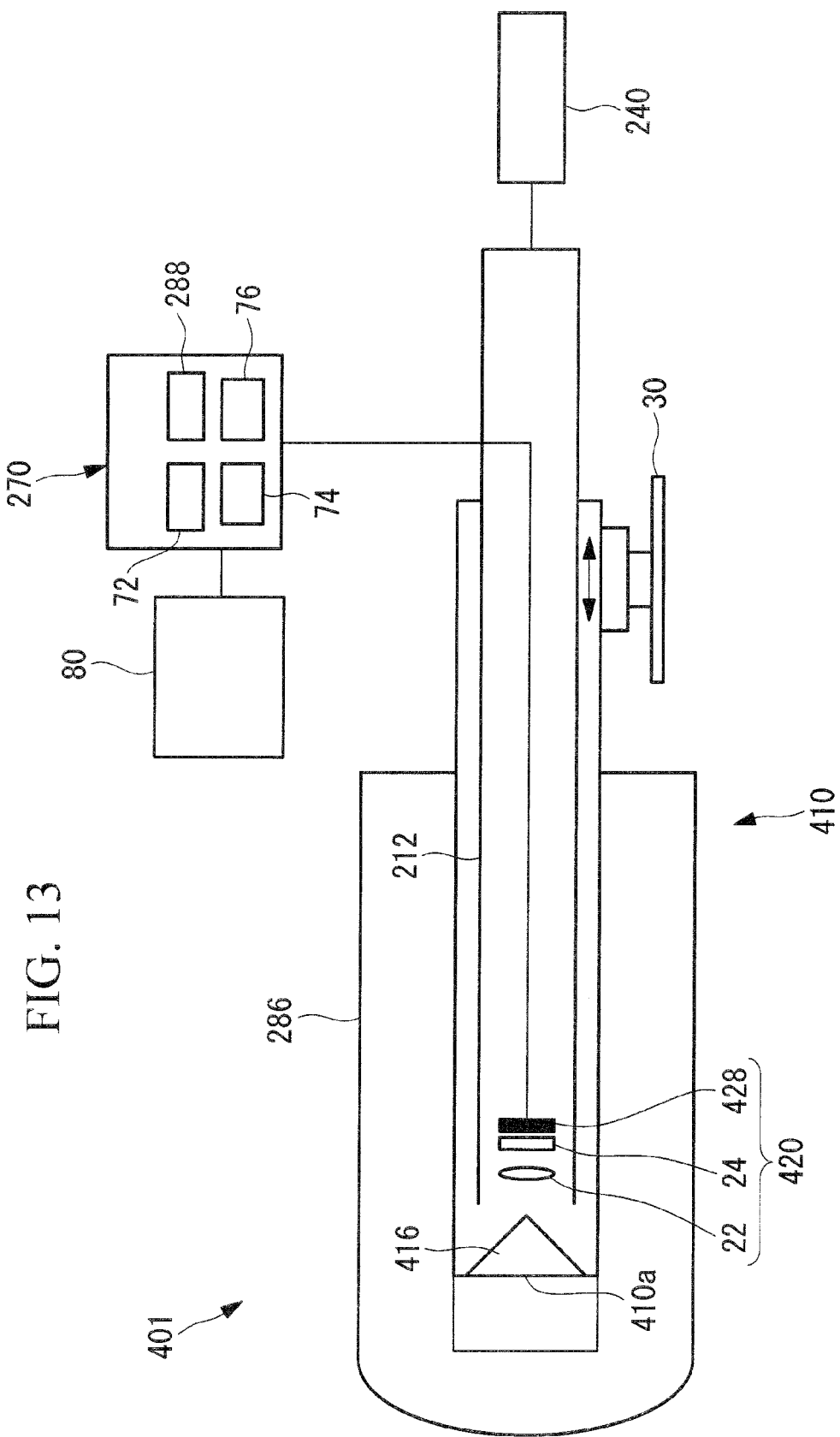
FIG. 13 is a schematic configuration diagram of a fluorescence observation apparatus according to a modification of the second embodiment of the present invention.

As an alternative to the fluorescence observation apparatus 201 described in terms of a scanning-type endoscopic device in this embodiment, for example, a fluorescence observation apparatus 401 may be a panorama-type endoscopic device that can acquire an entire circumferential image of the inner wall of the body cavity in the rectum at once, as shown in FIG. 13.

In this case, in place of the second collimator lens 214, the reflective mirror 216, and the rotating mechanism 218, an insertion section 410 may include a conical mirror 416 disposed at a tip 410a of the insertion section 410 and configured to reflect the excitation light, emitted from the illuminating device 240 and optically guided by the fiber 212, in a direction orthogonal to the light axis, and an image acquisition unit (image acquisition section) 420 that acquires an image of fluorescence generated at the inner wall of the body cavity as a result of the emission of the excitation light so as to acquire fluorescence image information. The image acquisition unit 420 may be constituted of an image-acquisition optical system 22, an excitation-light cut filter 24, and a CCD 428.

Figure 14:
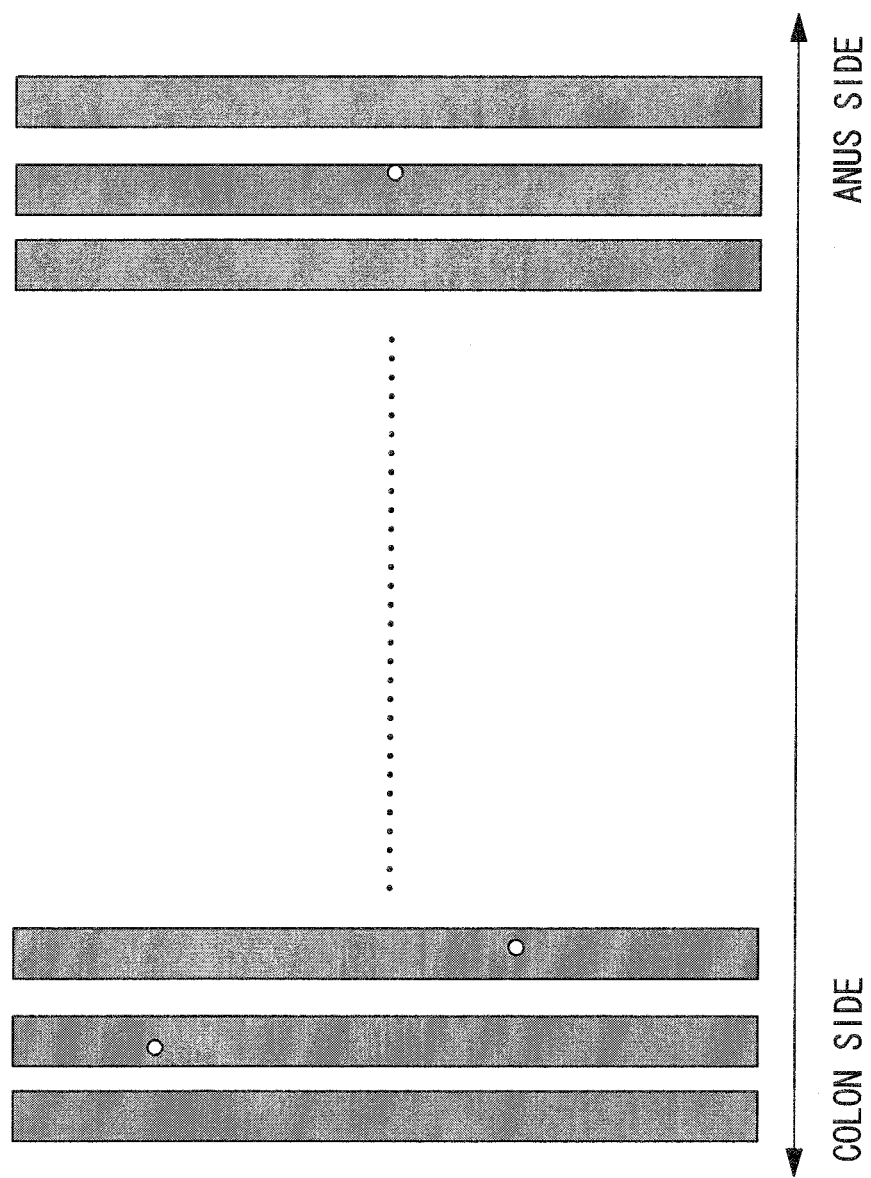
FIG. 14 is a diagram illustrating a composite image obtained by an image combining section in FIG. 13.

Regarding the fluorescence observation apparatus 401 having such a configuration, the insertion section 410 is inserted into the body cavity to which GST-π-sensitive fluorescent probes are applied in advance, and the excitation light emitted from the illuminating device 240 and optically guided by the fiber 212 is reflected by the conical mirror 416 so as to be emitted from a side surface of the insertion section 410 to the entire circumference of the inner wall of the body cavity in the rectum. Fluorescence generated at the inner wall of the body cavity is reflected by the conical mirror 416 so as to become incident on the image acquisition unit 420, whereby sets of fluorescence image information covering the entire circumference of the inner wall of the body cavity in the rectum are sequentially acquired. Then, the image combining section 288, for example, combines multiple panoramic fluorescence images, which display the inner wall in the entire circumference of the body cavity of the rectum, from the colon side toward the anus side of the rectum, as shown in FIG. 14, thereby acquiring a composite image. In this manner, the fluorescence image information can be acquired within a short time, and the configuration of the insertion section 410 can be further simplified, thereby achieving a narrower shape and weight reduction.

Third Embodiment

Next, a fluorescence observation apparatus according to a third embodiment of the present invention will be described.

Figure 15:
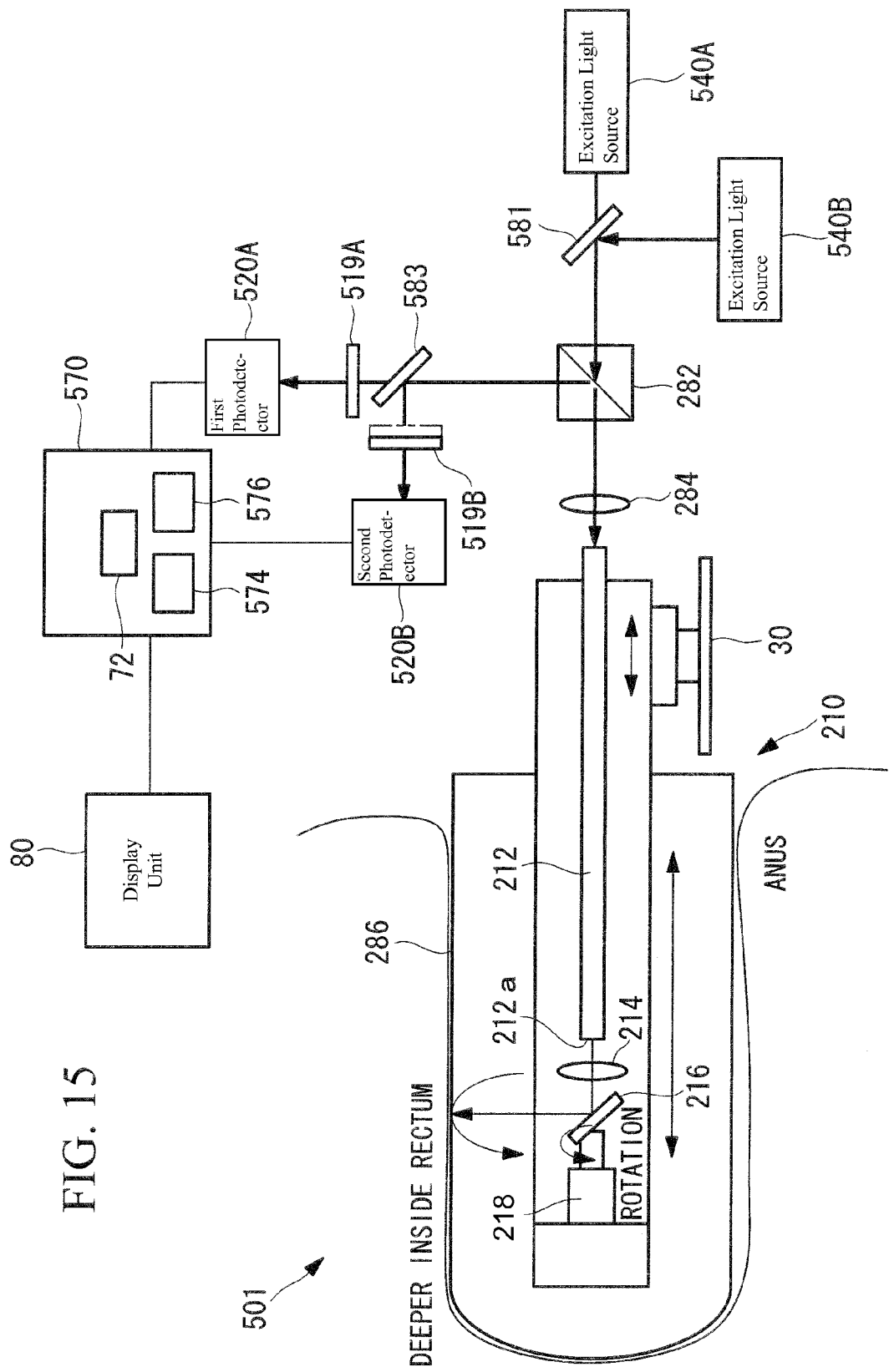
FIG. 15 is a schematic configuration diagram of a fluorescence observation apparatus according to a third embodiment of the present invention.

A fluorescence observation apparatus 501 according to this embodiment is a scanning-type endoscopic device and is configured to perform fluorescence observation by using a reference dye together with GST-π probes. As shown in FIG. 15, the fluorescence observation apparatus 501 includes an excitation light source (illuminating section) 540A that emits excitation light with a wavelength band of 480 nm, an excitation light source (illuminating section) 540B that emits excitation light (reference excitation light) with a wavelength band of 750 nm, a first dichroic mirror (DM) 581, a second dichroic mirror 583 that splits fluorescence generated by the excitation light from the excitation light source 540A and fluorescence generated by the excitation light from the excitation light source 540B from each other, a first PD (photodetector, image acquisition section) 520A and a second PD (photodetector, image acquisition section) 520B that respectively acquire images of the fluorescence split by the second dichroic mirror (DM) 583 so as to acquire fluorescence image information, and an image-information processing device 570 that processes the fluorescence image information acquired by the first PD 520A and the second PD 520B.

The image-information processing device 570 is provided with a counting section 72, an image generating section 574 that generates two-dimensional fluorescence images on the basis of the fluorescence image information acquired by the first PD 520A and the second PD 520B, and an image comparing section 576 that compares the generated fluorescence images. Reference numeral 519A denotes a first excitation-light cut filter, and reference numeral 519B denotes a second excitation-light cut filter.

In the following description, sections with the same configurations as those in the fluorescence observation apparatus 1 according to the first embodiment or the fluorescence observation apparatus 201 or 401 according to the second embodiment are given the same reference numerals, and descriptions thereof will be omitted.

Figure 16A:
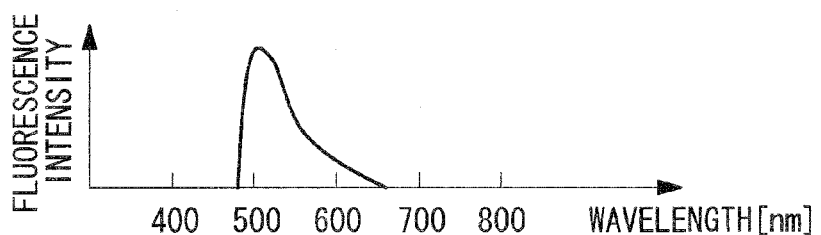
FIG. 16A illustrates a wavelength characteristic of a GST-π-probe fluorescence spectrum.
Figure 16B:
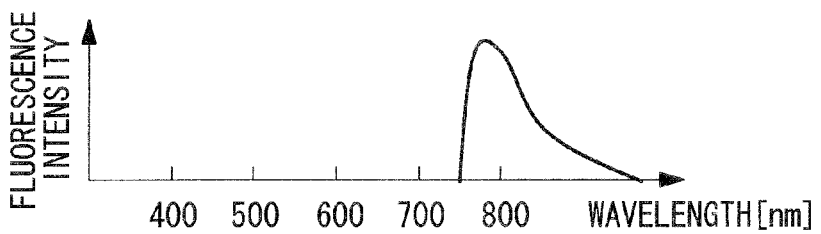
FIG. 16B illustrates a wavelength characteristic of a reference-dye fluorescence spectrum.
Figure 17A:
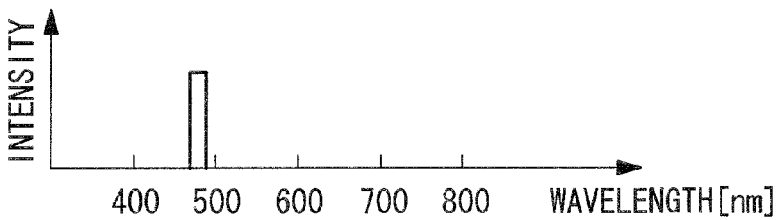
FIG. 17A illustrates a wavelength characteristic of excitation light emitted from a first excitation light source.
Figure 17B:
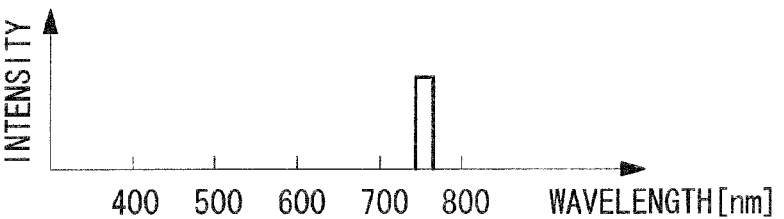
FIG. 17B illustrates a wavelength characteristic of excitation light emitted from a second excitation light source.
Figure 18A:
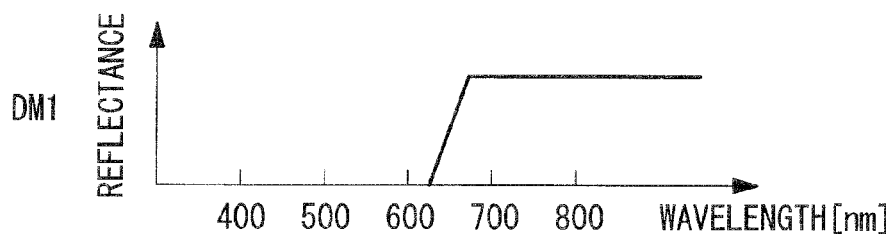
FIG. 18A illustrates a reflectance characteristic of a first dichroic mirror.
Figure 18B:
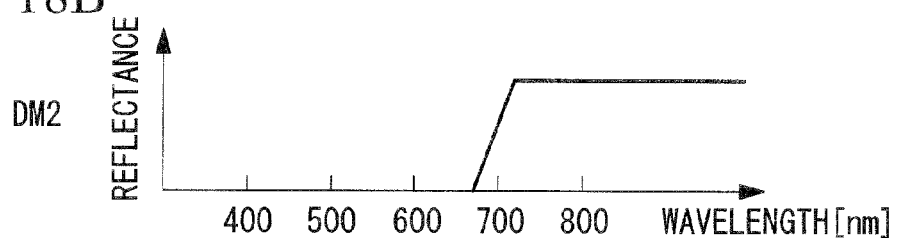
FIG. 18B illustrates a reflectance characteristic of a second dichroic mirror.
Figure 19A:
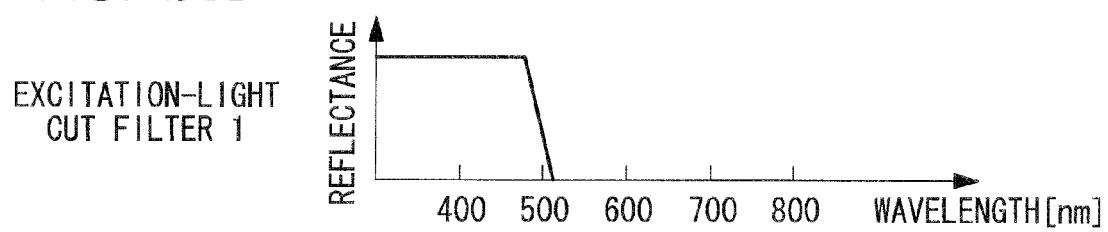
FIG. 19A illustrates a reflectance characteristic of a first excitation-light cut filter.
Figure 19B:
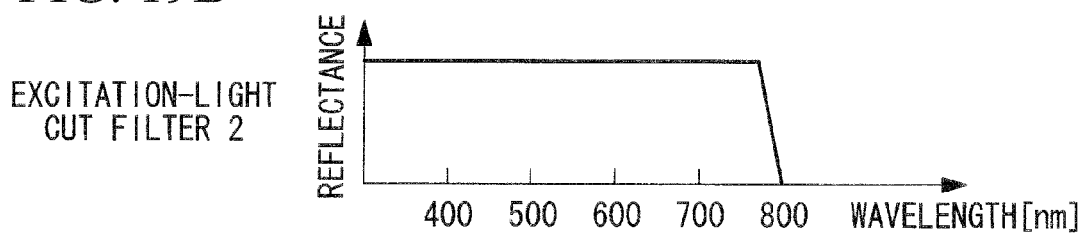
FIG. 19B illustrates a reflectance characteristic of a second excitation-light cut filter.

In this embodiment, for example, the GST-π-probe fluorescence spectrum has the wavelength characteristic shown in FIG. 16A, and the reference-dye fluorescence spectrum has the wavelength characteristic shown in FIG. 16B. The excitation light emitted from the excitation light source 540A has the wavelength characteristic shown in FIG. 17A, and the excitation light emitted from the excitation light source 540B has the wavelength characteristic shown in FIG. 17B. The first dichroic mirror 581 has the reflectance characteristic shown in FIG. 18A, and the second dichroic mirror 583 has the reflectance characteristic shown in FIG. 18B. The first excitation-light cut filter 519A has the reflectance characteristic shown in FIG. 19A, and the second excitation-light cut filter 519B has the reflectance characteristic shown in FIG. 19B.

When the GST-π probes are applied to the inner wall of the body cavity of the rectum, there are two kinds of areas where the fluorescence emits with high intensity, i.e., increased GST-π areas (increased expression level or increased activity) and areas where the dye tends to accumulate easily. For example, when there are dead cells (i.e., cells detached from the rectum surface) or the like, the dye may sometimes get trapped in these dead cells and emit. Since GST-π also exists in normal areas, it is not only the ACF that emit. ACF emit fluorescence easily simply because there is a large amount of GST-π therein, and when there is a large amount of dye accumulated in other areas, fluorescence emitting with high intensity is also observed in these dye-accumulated areas. For example, an inflated area or the like may sometimes emit since the dye itself can easily penetrate the cells thereof.

Regarding the fluorescence observation apparatus 501 having such a configuration, the GST-π probes are applied to the inside of the body cavity together with the reference dye (IR-780) and are then removed after several minutes, and subsequently, excitation light rays are simultaneously emitted from the excitation light source 540A and the excitation light source 540B onto the inner wall of the body cavity. Fluorescence generated at the inner wall of the body cavity is optically guided by the fiber 212 and is reflected by the beam splitter 282 before being split by the second dichroic mirror 583. The fluorescence from the GST-π probes travels through the first excitation-light cut filter 519A before an image of the fluorescence is acquired by the first PD 520A, whereas the fluorescence from reference probes travels through the second excitation-light cut filter 519B before an image of the fluorescence is acquired by the second PD 520B.

Figure 20B:
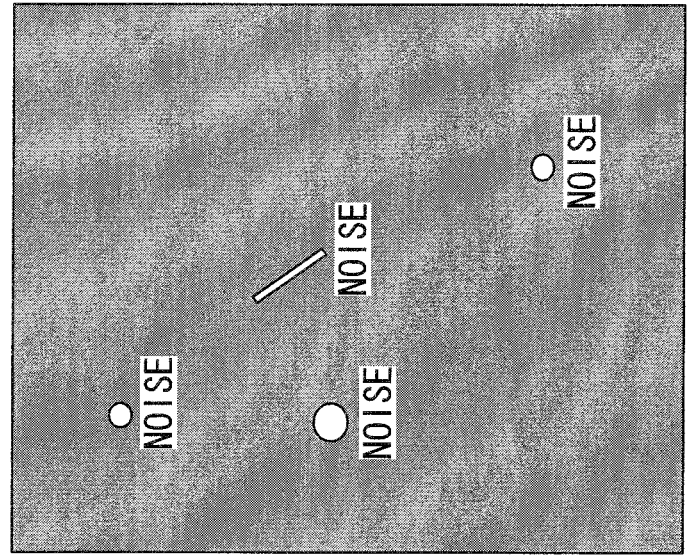
FIG. 20B illustrates a fluorescence image corresponding to reference probes.
Figure 20A:
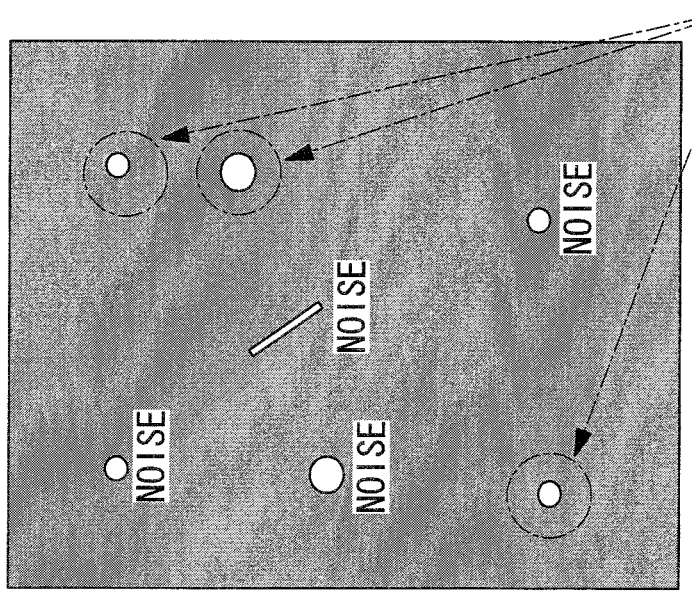
FIG. 20A illustrates a fluorescence image corresponding to GST-π probes.

In the image-information processing device 570, the image generating section 574 generates a fluorescence image, as shown in FIG. 20A, on the basis of the fluorescence image information acquired by the first PD 520A and also generates a fluorescence image, as shown in FIG. 20B, on the basis of the fluorescence image information acquired by the second PD 520B.

As shown in FIG. 20A, the fluorescence image (referred to as "fluorescence image A" hereinafter) corresponding to the GST-πprobes has two kinds of bright spots, that is, bright spots of ACF and bright spots of noise (i.e., areas where the dye tends to accumulate easily). On the other hand, as shown in FIG. 20B, the fluorescence image (referred to as "fluorescence image B" hereinafter) corresponding to the reference probes only has bright spots of noise. The image comparing section 576 compares the fluorescence image A and the fluorescence image B with each other, and the counting section 72 counts the number of bright spots existing only in the fluorescence image A so that only the number of ACF can be counted.

Although the image-information processing device 570 includes the image comparing section 576 in this embodiment, for example, the image comparing section 576 may be omitted, and the image generating section 574 may be configured to perform correction, such as subtraction processing or division processing, on the fluorescence image A on the basis of the fluorescence image B. In this manner, the fluorescence image can be made to have noise removed therefrom so as to have only ACF therein, whereby the number of ACF can be accurately counted.

Fourth Embodiment

Next, a fluorescence observation apparatus according to a fourth embodiment of the present invention will be described.

Figure 21:
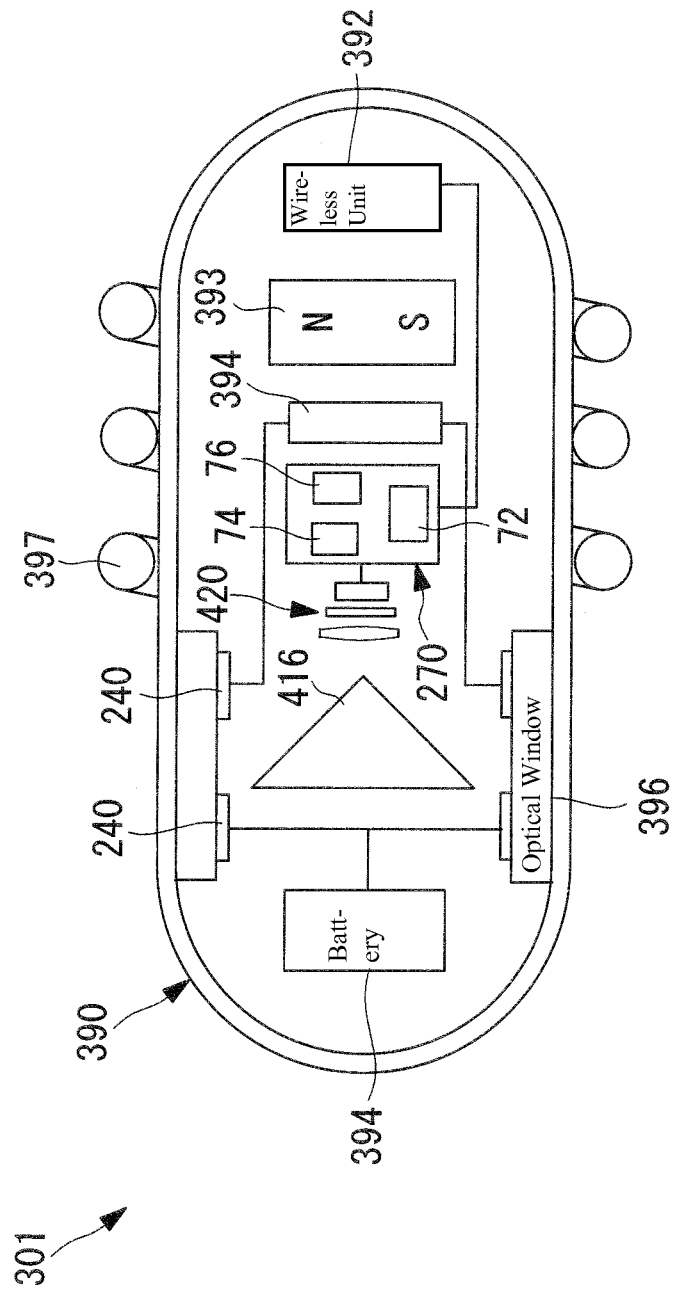
FIG. 21 is a schematic configuration diagram of a fluorescence observation apparatus according to a fourth embodiment of the present invention.

As shown in FIG. 21, a fluorescence observation apparatus 301 according to this embodiment is a capsule-type endoscopic device and has a capsule sheath 390 formed in a capsule shape that encapsulates an illuminating device 240, a conical mirror 416, an image acquisition unit 420, an image-information processing device 270, a wireless unit 392 that sends fluorescence image information acquired by the image acquisition unit 420 to the outside, a permanent magnet 393, and a battery 394 that supplies power to the illuminating device 240 and the like.

In the following description, sections with the same configurations as those in the fluorescence observation apparatus 1 according to the first embodiment, the fluorescence observation apparatus 201 or 401 according to the second embodiment, or the fluorescence observation apparatus 501 according to the third embodiment are given the same reference numerals, and descriptions thereof will be omitted.

The permanent magnet 393 has, for example, a columnar shape with its column halves magnetized to an N-pole and an S-pole, respectively, and the magnetic poles are fixed in a direction orthogonal to the longitudinal axis of the capsule shape.

The outer peripheral surface of the capsule sheath 390 is provided with an optical window 396 formed along the periphery in the longitudinal direction and a propelling mechanism (moving mechanism) 397 formed of a wire, circular in cross section, helically wound around the longitudinal axis. Emission of excitation light and detection of fluorescence are performed via the optical window 396. The propelling mechanism 397 converts rotation of the fluorescence observation apparatus 301 around the longitudinal axis into propelling motion.

The operation of the fluorescence observation apparatus 301 having such a configuration will now be described.

The fluorescence observation apparatus 301 is inserted through the anus and into the rectum to which GST-π-sensitive fluorescent probes are applied in advance, and is sent to the sigmoid. When an external magnetic field rotating around the longitudinal axis is applied to the fluorescence observation apparatus 301, the propelling mechanism 397 causes the fluorescence observation apparatus 301 to move linearly while rotating around the longitudinal axis.

As the fluorescence observation apparatus 301 moves inside the rectum, excitation light emitted from the illuminating device 240 is transmitted through the optical window 396 so as to be emitted onto the inner wall of the body cavity, and fluorescence generated at the inner wall of the body cavity is reflected by a conical mirror 416 via the optical window 396 so as to become incident on the image acquisition unit 420. Fluorescence image information of the inner wall of the body cavity is acquired by the image acquisition unit 420 and is image-processed in the image-information processing device 270.

A counting section 72 counts the number of ACF, and the wireless unit 392 continuously wirelessly-transmits the fluorescence image information, the counted-number result, and the like to a receiver (not shown) disposed outside the biological organism. The fluorescence observation apparatus 301 is expelled outward from the biological organism through the anus. For example, an external device (not shown) disposed outside the biological organism may display the ACF by retrieving the fluorescence image information from the receiver.

The fluorescence observation apparatus 301 may include a storage section that stores the fluorescence image information acquired by the image acquisition unit 420 so that, after the fluorescence observation apparatus 301 is expelled from the body cavity, the fluorescence image information can be transmitted to the receiver from the wireless unit 392 or the fluorescence image information can be transferred to the external device by removing the storage section from the capsule sheath 390.

Although the counting section 72 is disposed within the capsule sheath 390 in this embodiment, a capsule endoscopic system may be formed by disposing the counting section 72 in the external device.

Although the embodiments of the present invention have been described above in detail with reference to the drawings, specific configurations are not to be limited to the embodiments, and the present invention may include design modifications so long as they do not depart from the spirit of the invention. For example, the present invention is not limited to the embodiments and the modifications described above and may be applied to embodiments achieved by appropriately combining these embodiments and modifications; it is not limited in particular.

Furthermore, for example, although each ACF is classified in accordance with the fluorescence intensity, the size, or the pattern in each of the above embodiments, the ACF may be classified in accordance with a combination of the fluorescence intensity, the size, and the pattern.

Furthermore, for example, in each of the above embodiments, although the GST-π-sensitive fluorescent probes are described as an example of fluorescent probes for making the ACF sites emit with high intensity, it is possible to use fluorescent probes whose fluorescence characteristics change by reacting with a molecule (e.g., iNOS (nitric oxide synthase)) abundantly existing in each ACF or fluorescent probes whose fluorescence characteristics change by reacting with a product produced by activation of the molecule (e.g., NO (nitric oxide) produced by activation of iNOS if the molecule is iNOS).

In addition to the GST-π (glutathione-S-transferase pi) and the iNOS (nitric oxide synthase 2, inducible) mentioned above, examples of the molecule existing in the ACF include cyclin D1, cox-2 (prostaglandin-endoperoxide synthase 2), β-catenin (catenin, beta-1), CD44 (CD44 molecule), EGFR (Epidermal Growth Factor Receptor), p53 (tumor protein p53), mdm2 (Mdm2 p53 binding protein homolog), PCNA (proliferating cell nuclear antigen), TGF-β (transforming growth factor, beta-1), ErbB2 (v-erb-b2 erythroblastic leukemia viral oncogene homolog 2), APC (adenomatous polyposis coli), CEA (pregnancy specific beta-1-glycoprotein 2), p-cad (p-cadherin), Cdh1 (Cadherin 1), p16INK4a (cyclin-dependent kinase inhibitor 2A), met (met proto-oncogene), c-fos (FBJ murine osteosarcoma viral oncogene homolog), Fzd1 (Frizzled homolog 1), Ctsb (Cathepsin B), and Ctnnb (Catenin beta). The molecule may be one or more of these examples.

The molecule is, for example, DNA, RNA, protein, peptide, lipid, or sugar. Particularly suitable is mRNA or protein, the amount of which occurring in an ACF increases or decreases.

By using the fluorescent probes whose fluorescence characteristics change by reacting with a molecule, a molecule abundantly occurring in an ACF can be directly detected. If the molecule is protein, a fluorescence-labeled antibody may be used. The fluorescence-labeled antibody may be prepared by a known method. If the molecule is a nucleic acid, such as mRNA, a nucleic acid with a sequence complementary to the aforementioned nucleic acid may be fluorescence-labeled by a known method and may be used as the fluorescent probes. Alternatively, the ligand of the target molecule may be used as the fluorescent probes. On the other hand, by using the fluorescent probes whose fluorescence characteristics change by reacting with a product produced by activation of a molecule, the existence of the molecule in an ACF can be indirectly detected. Alternatively, by employing a known method, a substrate acting as the target of the molecule may be used as the fluorescent probes.

REFERENCE SIGNS LIST 1, 201, 301, 401, 501 fluorescence observation apparatus
20, 420 image acquisition unit (image acquisition section)
30 position control unit (moving mechanism)
40 light source unit (illuminating section)
72 counting section
220 PD (image acquisition section)
240 illuminating device (illuminating section)
397 propelling mechanism (moving mechanism)
574 image generating section

The invention claimed is:

1. A fluorescence observation apparatus comprising:
an illuminator that is adapted to be inserted into a body cavity of a biological organism and that is adapted to emit excitation light onto an inner wall of the body cavity;
an image acquirer that acquires an image of fluorescence generated by the excitation light emitted from the illuminator so as to acquire image information; and
a processor, the processor programmed to count the number of fluorescence generation sites, which are sites existing in the inner wall of the body and are generating fluorescence, having at least a predetermined fluorescence intensity on the basis of the fluorescence intensity included in the image information acquired by the image acquirer, the fluorescence generation sites being generated when a fluorescent probe whose fluorescence characteristic changes by reacting with a predetermined molecule present in the inner wall of the body cavity is excited or when a fluorescent probe whose fluorescence characteristic changes by reacting with a product produced by activation of the molecule is excited.

2. The fluorescence observation apparatus according to claim 1, further comprising a moving mechanism configured to move the illuminator and the image acquirer relative to the inner wall of the body cavity.

3. The fluorescence observation apparatus according to claim 2, further comprising an image combiner that obtains a composite image by combining multiple sets of image information acquired by the image acquirer while moving the image acquirer using the moving mechanism,
wherein the processor counts the number of fluorescence generation sites with predetermined brightness or higher within the composite image obtained by the image combiner.

4. The fluorescence observation apparatus according to claim 2, wherein the processor is programmed to add a reference line to the image information acquired by the image acquirer, and
wherein when the image acquirer is moved by the moving mechanism, the processor counts the number of fluorescence generation sites that cross over the reference line within the image information acquired by the image acquirer.

5. The fluorescence observation apparatus according to claim 1, further comprising a fluorescent-probe discharger that is adapted to apply one or more of a fluorescent probe to the inner wall of the body cavity.

6. The fluorescence observation apparatus according to claim 5, wherein the fluorescence-probe discharger applies one or more of the fluorescent probes whose fluorescence characteristic changes by reacting with the predetermined molecule present in an Aberrant Crypt Focus (ACF).

7. The fluorescence observation apparatus according to claim 1, wherein the processor counts the number of fluorescence generation sites existing in an area between 0.4 and 0.8 from the center of the image based on the image information acquired by the image acquirer when the distance from the center to an edge of the image is defined as 1.

8. The fluorescence observation apparatus according to claim 1, further comprising:
a fluorescence-intensity measurer that measures the fluorescence intensity at each fluorescence generation site; and a fluorescence-intensity classifier that classifies the number of fluorescence generation sites counted by the processor in accordance with the fluorescence intensity at each fluorescence generation site measured by the fluorescence-intensity measurer.

9. The fluorescence observation apparatus according to claim 1, further comprising:
a fluorescence-size measurer that measures the size of each fluorescence generation site; and
a fluorescence-size classifier that classifies the number of fluorescence generation sites counted by the processor in accordance with the size of each fluorescence generation site measured by the fluorescence-size measurer.

10. The fluorescence observation apparatus according to claim 1, further comprising:
a fluorescence-pattern determiner that detects a pattern of each fluorescence generation site and determines whether or not the pattern matches a pattern of an Aberrant Crypt Focus (ACF) in which the predetermined molecule is present; and
a corrector that subtracts the number of fluorescence generation sites determined as not satisfying a pattern condition of the ACF by the fluorescence-pattern determiner from the number of fluorescence generation sites counted by the processor.

11. The fluorescence observation apparatus according to claim 1, further comprising:
an image generator that generates a two-dimensional image of the fluorescence generation sites counted by the processor; and
a pattern classifier that classifies each fluorescence generation site in accordance with a pattern thereof on the basis of the two-dimensional image generated by the image generator.

12. The fluorescence observation apparatus according to claim 1, wherein the illuminator emits reference excitation light having a wavelength characteristic different from that of the excitation light, and
wherein the fluorescence observation apparatus further comprises an image generator that generates a two-dimensional fluorescence image and a two-dimensional reference fluorescence image on the basis of the image information corresponding to the excitation light and image information corresponding to the reference excitation light that are acquired by the image acquirer, and that corrects the fluorescence image acquired using the excitation light by using the reference fluorescence image acquired using the reference excitation light.

13. The fluorescence observation apparatus according to claim 1, wherein the predetermined molecule is present in an Aberrant Crypt Focus (ACF) formed on the inner wall of the body cavity.

14. The fluorescence observation apparatus according to claim 13, wherein the molecule is at least one of cyclin-D1, cox-2, β-catenin, iNOS, CD44, EGFR, Fzd1, and GST-π.

15. A fluorescence observation apparatus comprising:
an illuminating means for emitting excitation light onto an inner wall of a body cavity of a biological organism, the illuminating means adapted to be inserted into the body cavity;
an image acquiring means for acquiring an image of fluorescence generated by the excitation light emitted from the illuminating means so as to acquire image information; and
a processor, the processor programmed to count the number of fluorescence generation sites, existing in the inner wall of the body, having at least a predetermined fluorescence intensity on the basis of the fluorescence intensity included in the image information acquired by the image acquiring means, the fluorescence generation sites being generated when a fluorescent probe whose fluorescence characteristic changes by reacting with a predetermined molecule present in the inner wall of the body cavity is excited or when a fluorescent probe, whose fluorescence characteristic changes by reacting with a product produced by activation of the predetermined molecule, is excited.

16. A fluorescence observation method comprising:
emitting excitation light onto an inner wall of a body cavity of a biological organism;
acquiring an image of fluorescence generated by the emitted excitation light; and
counting the number of fluorescence generation sites with a processor programmed to count the number of fluorescence generation sites, present in the inner wall of the body, having at least a predetermined fluorescence intensity on the basis of the fluorescence intensity included in acquired image information, the fluorescence generation sites being generated when a fluorescence probe whose fluorescence characteristic changes by reacting with a predetermined molecule present in the inner wall of the body cavity is excited or when a fluorescent probe whose fluorescence characteristic changes by reacting with a product produced by activation of the predetermined molecule is excited.

17. The fluorescence observation method of claim 16, wherein the predetermined molecule is present in an Aberrant Crypt Focus (ACF) formed on the inner wall of the body cavity.

18. The fluorescence observation method according to claim 17, wherein the molecule is at least one of cyclin-D1, cox-2, β-catenin, iNOS, CD44, EGFR, Fzd1, and GST-π.

19. The fluorescence observation method according to claim 16, wherein the number of fluorescence generation sites existing in an area between 0.4 and 0.8 from the center of the image based on the acquired image information is counted when the distance from the center to an edge of the image is defined as 1.

20. The fluorescence observation method according to claim 16, further comprising:
measuring the fluorescence intensity at each fluorescence generation site; and
classifying the number of fluorescence generation sites being counted in accordance with the fluorescence intensity at each measured fluorescence generation site.

* * * * *